(12) United States Patent
Duffield et al.

(10) Patent No.: US 10,398,573 B2
(45) Date of Patent: Sep. 3, 2019

(54) INSERTION TOOL FOR IMPLANT AND METHODS OF USE

(71) Applicant: Institute for Musculoskeletal Science and Education, Ltd., Wayne, PA (US)

(72) Inventors: William Duffield, Collegeville, PA (US); James A. Sack, Elverson, PA (US)

(73) Assignee: Institute For Musculoskeletal Science And Education, Ltd., Wayne, PA (US)

( * ) Notice: Subject to any disclaimer, the term of this patent is extended or adjusted under 35 U.S.C. 154(b) by 426 days.

(21) Appl. No.: 15/291,732

(22) Filed: Oct. 12, 2016

(65) Prior Publication Data

US 2017/0100260 A1 Apr. 13, 2017

Related U.S. Application Data

(60) Provisional application No. 62/240,447, filed on Oct. 12, 2015.

(51) Int. Cl.
*A61F 2/46* (2006.01)
*A61F 2/44* (2006.01)
*A61B 90/00* (2016.01)

(52) U.S. Cl.
CPC .......... *A61F 2/4611* (2013.01); *A61F 2/4455* (2013.01); *A61B 2090/034* (2016.02); *A61B 2090/036* (2016.02); *A61B 2090/062* (2016.02); *A61F 2/442* (2013.01); *A61F 2002/4622* (2013.01); *A61F 2002/4623* (2013.01); *A61F 2002/4627* (2013.01); *A61F 2002/4629* (2013.01); *A61F 2002/4681* (2013.01)

(58) Field of Classification Search
CPC ...................................... A61F 2/4611
See application file for complete search history.

(56) References Cited

U.S. PATENT DOCUMENTS

2012/0150241 A1* 6/2012 Ragab ............... A61F 2/4611
606/86 A
2013/0079783 A1* 3/2013 Bertagnoli ......... A61B 17/1671
606/87

* cited by examiner

*Primary Examiner* — Andrew Yang
(74) *Attorney, Agent, or Firm* — Plumsea Law Group, LLC

(57) ABSTRACT

A multi-component implant insertion system for insertion of an intervertebral implant cage and methods of use thereof are described herein. Preferably, the proximal end of a hollow jaw is inserted into the distal end of an inserter. Once inside the inserter, a thread on the jaw engages a corresponding thread inside the inserter, allowing axial advancement of the jaw along the inserter. A ram is inserted through the proximal end of the jaw until the distal end of the ram protrudes at the distal end of the inserter assembly. Optionally, an adjustable stop introduced onto the superior portion of the inserter allows for control over the depth of insertion of the implant. An implant of appropriate size is introduced to the jaw of the inserter assembly and the implant/inserter assembly can be impacted into the vertebral body until the adjustable stop contacts the anterior edge of the vertebral body.

25 Claims, 24 Drawing Sheets

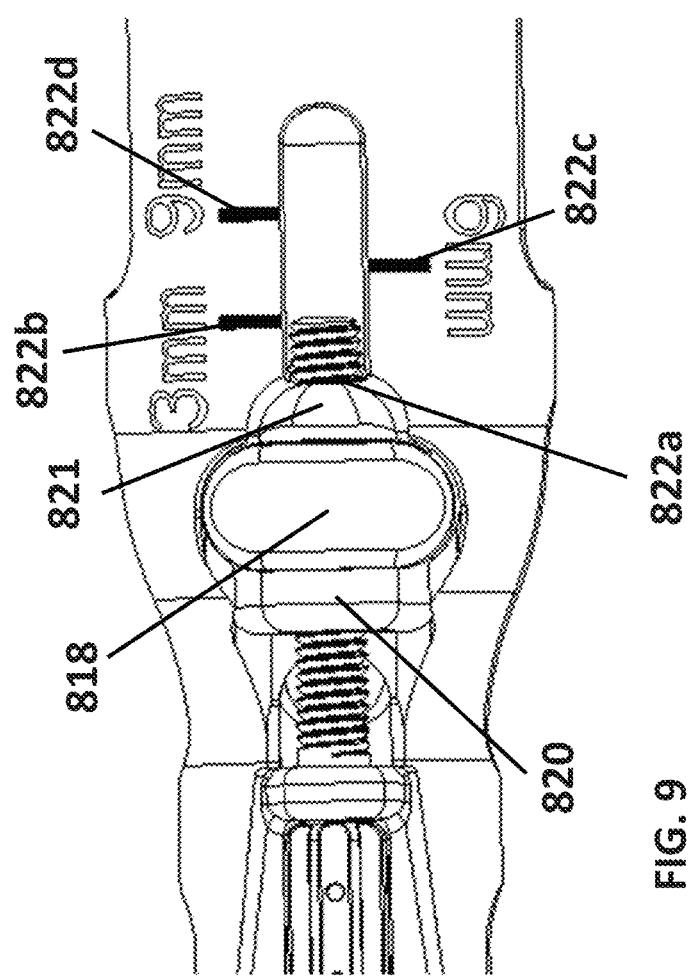

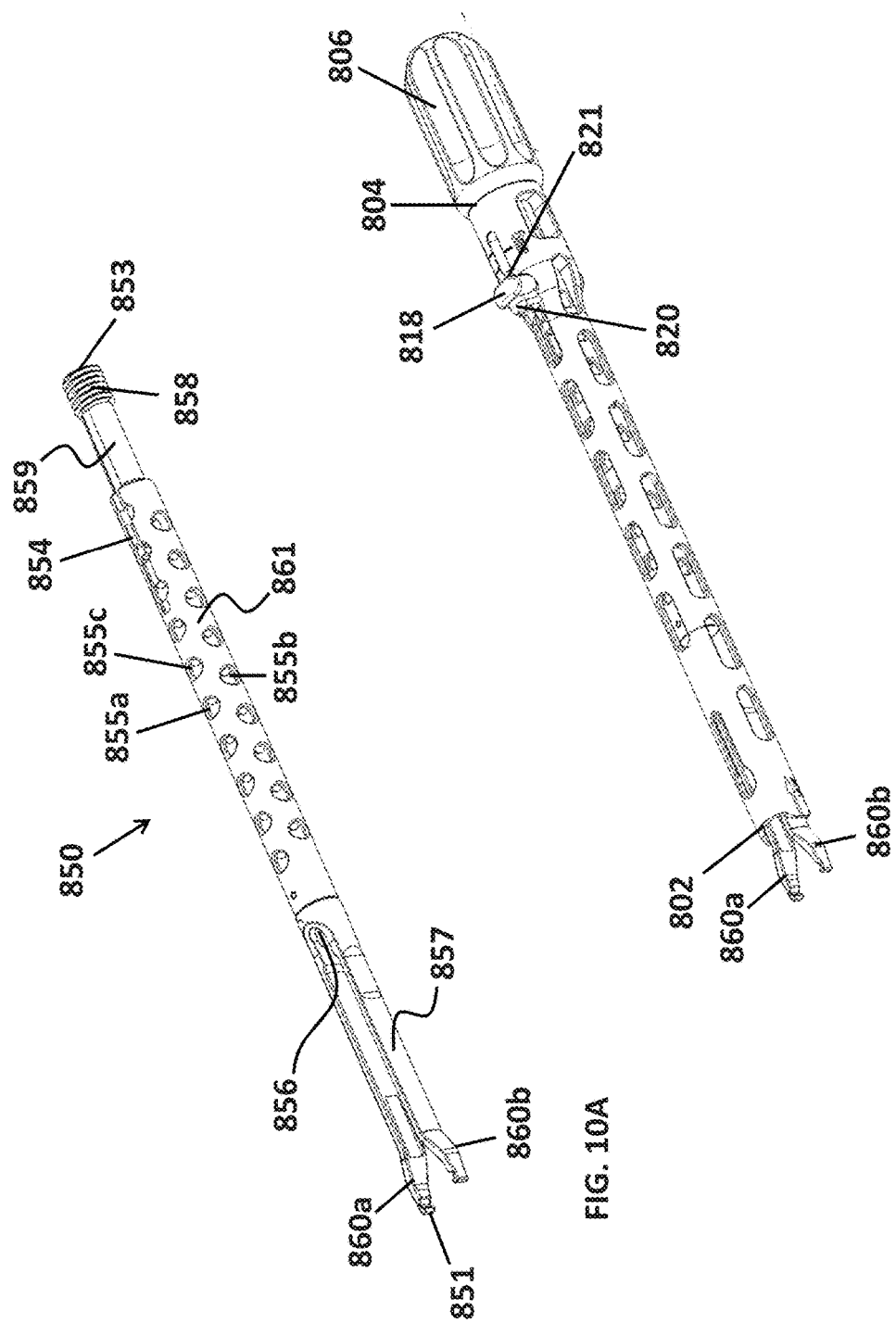

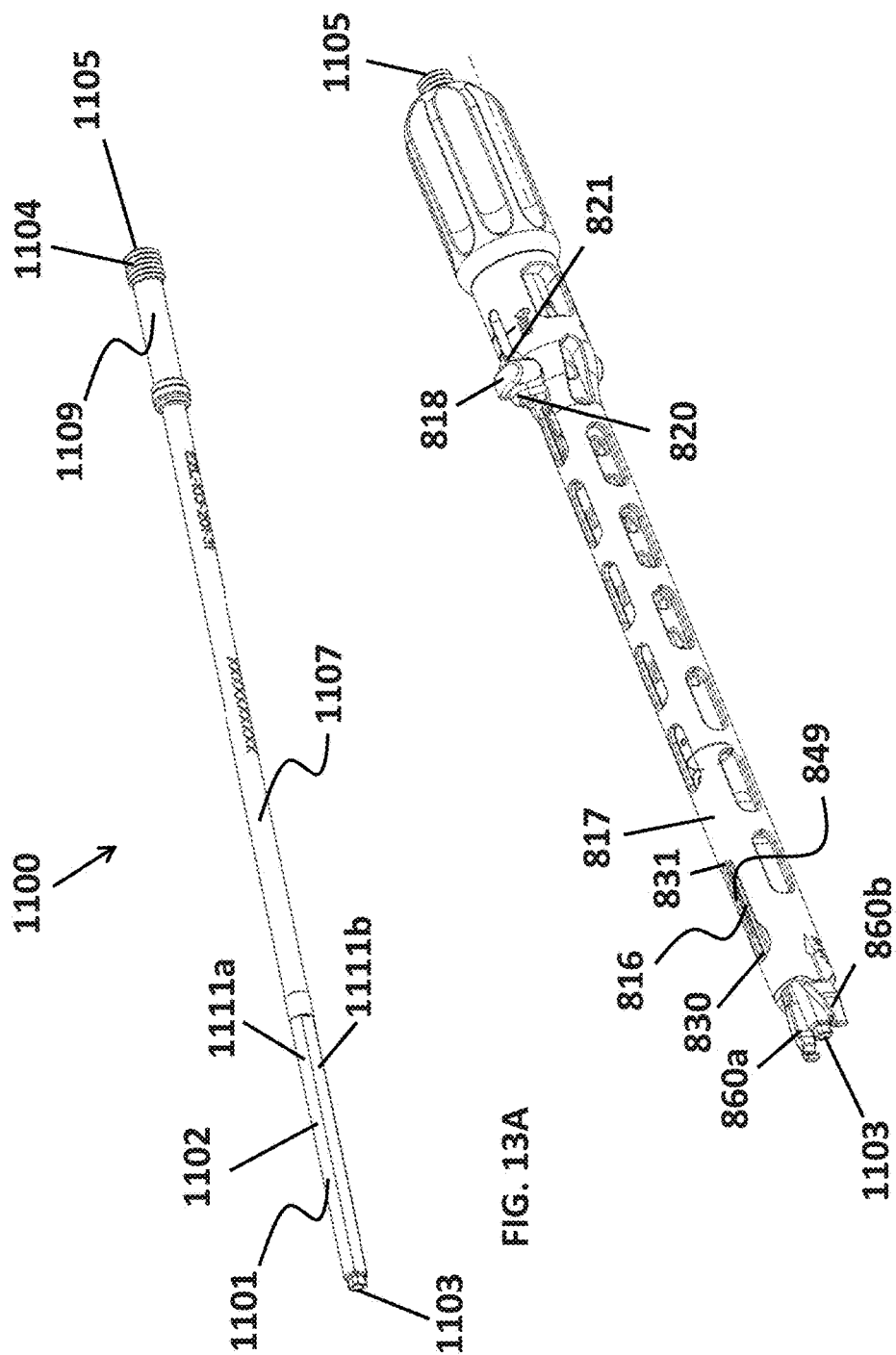

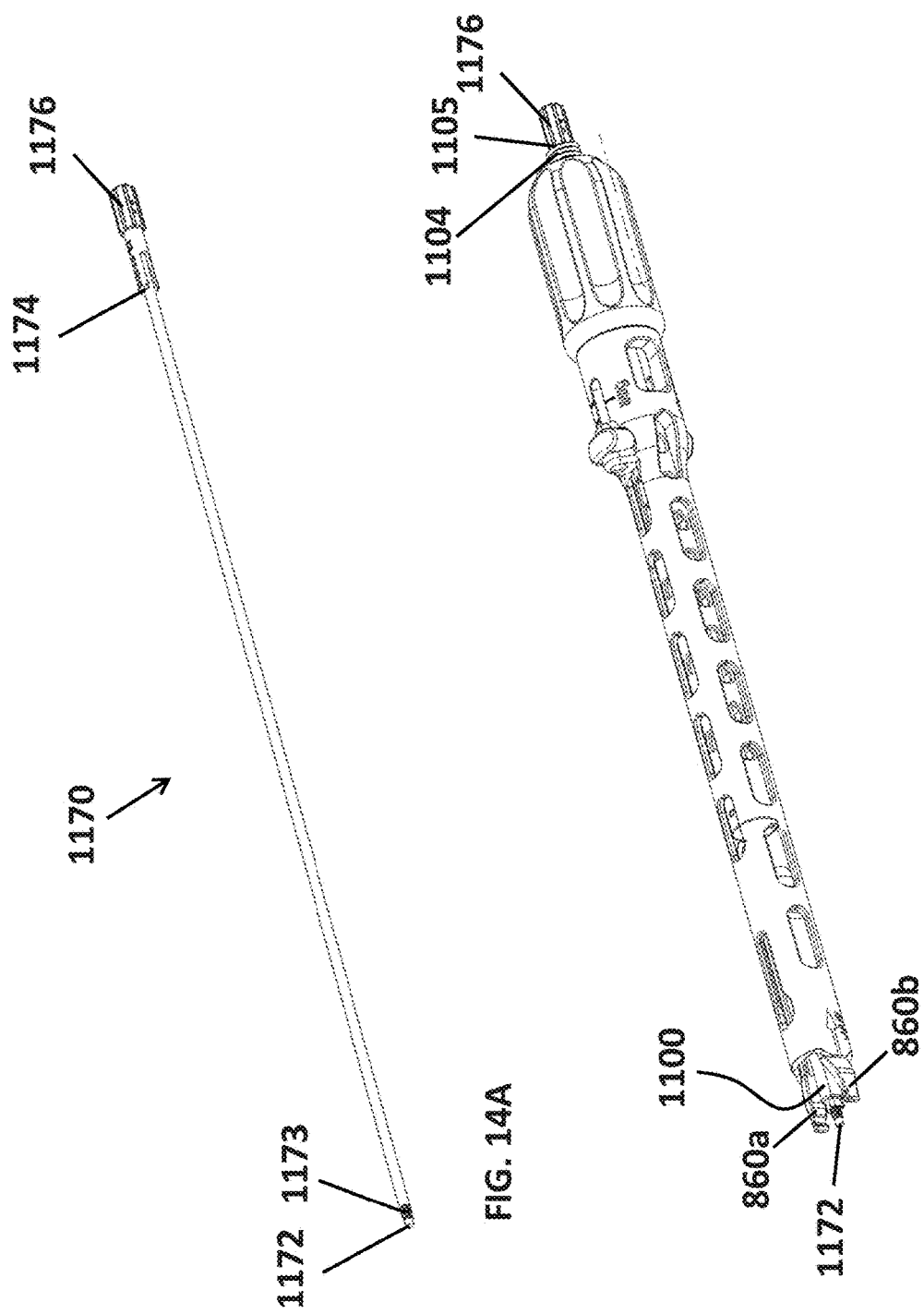

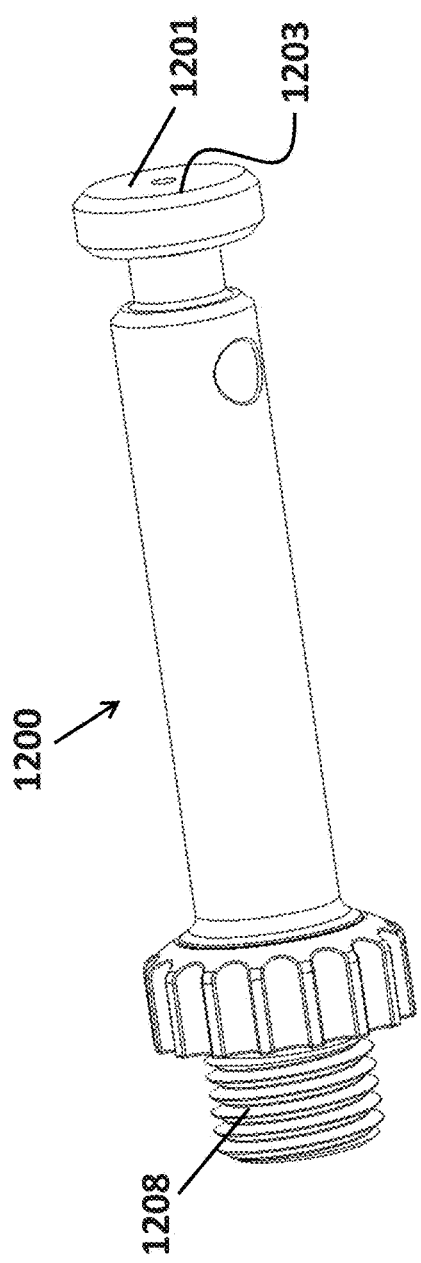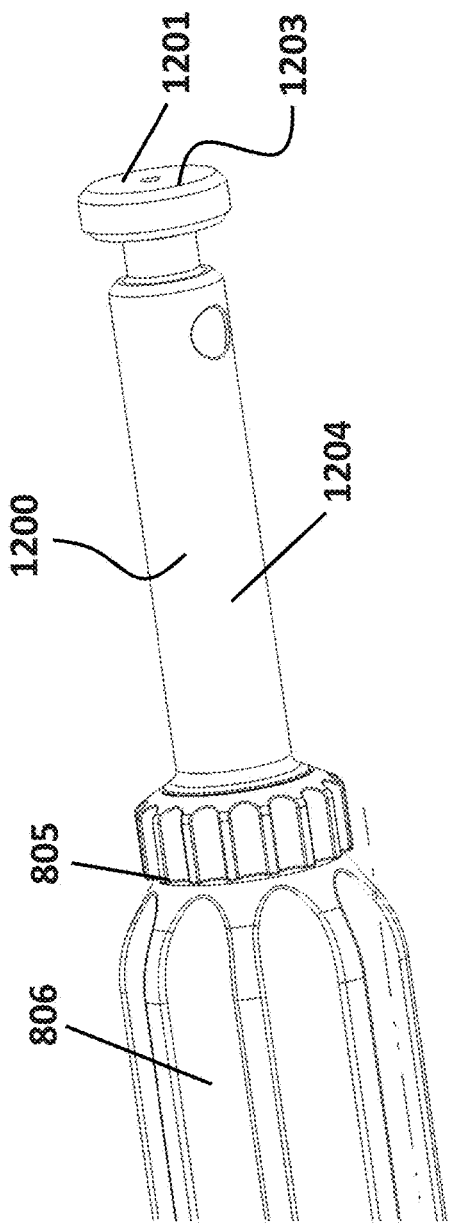
FIG. 17A
FIG. 17B

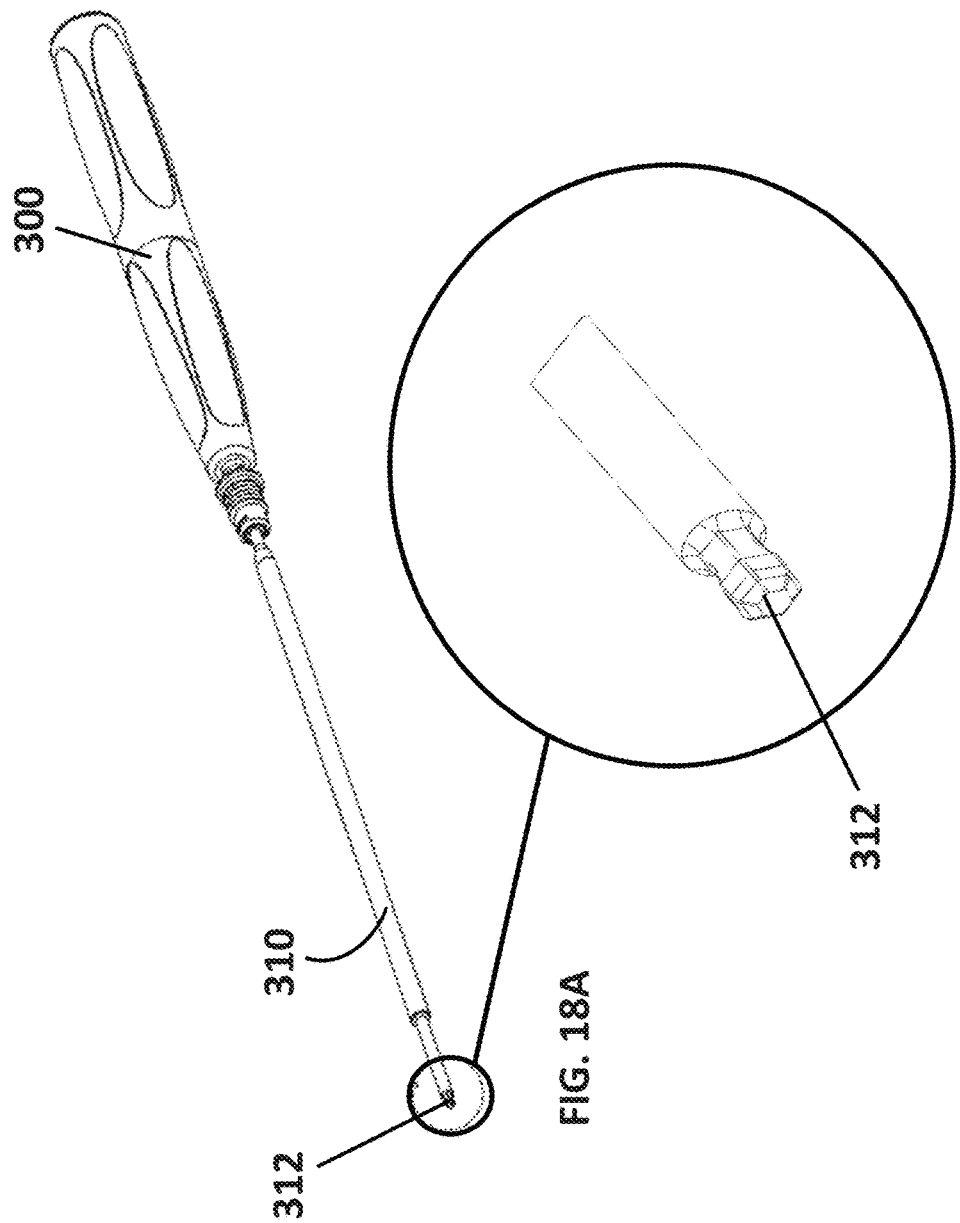

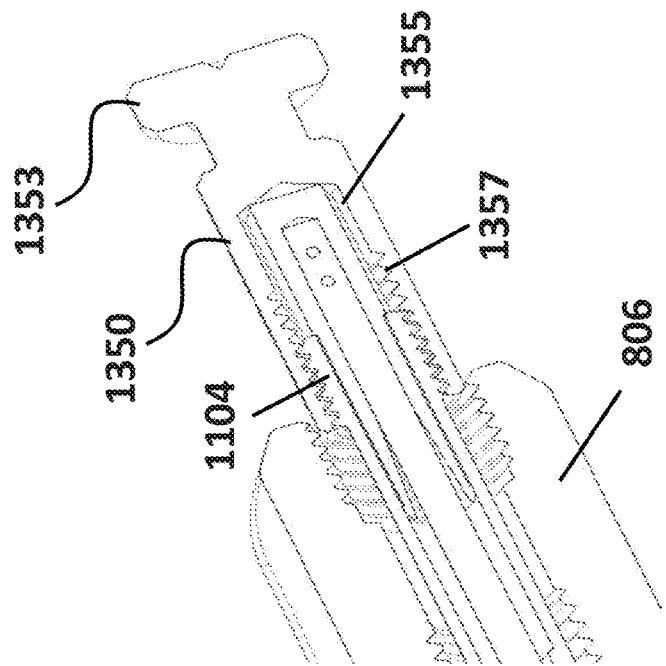
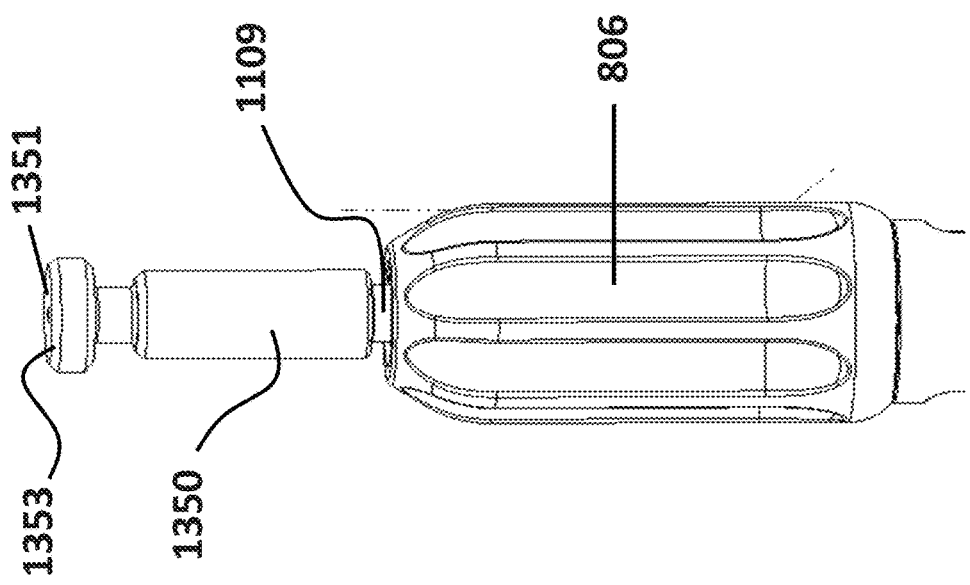
FIG. 21B
FIG. 21A

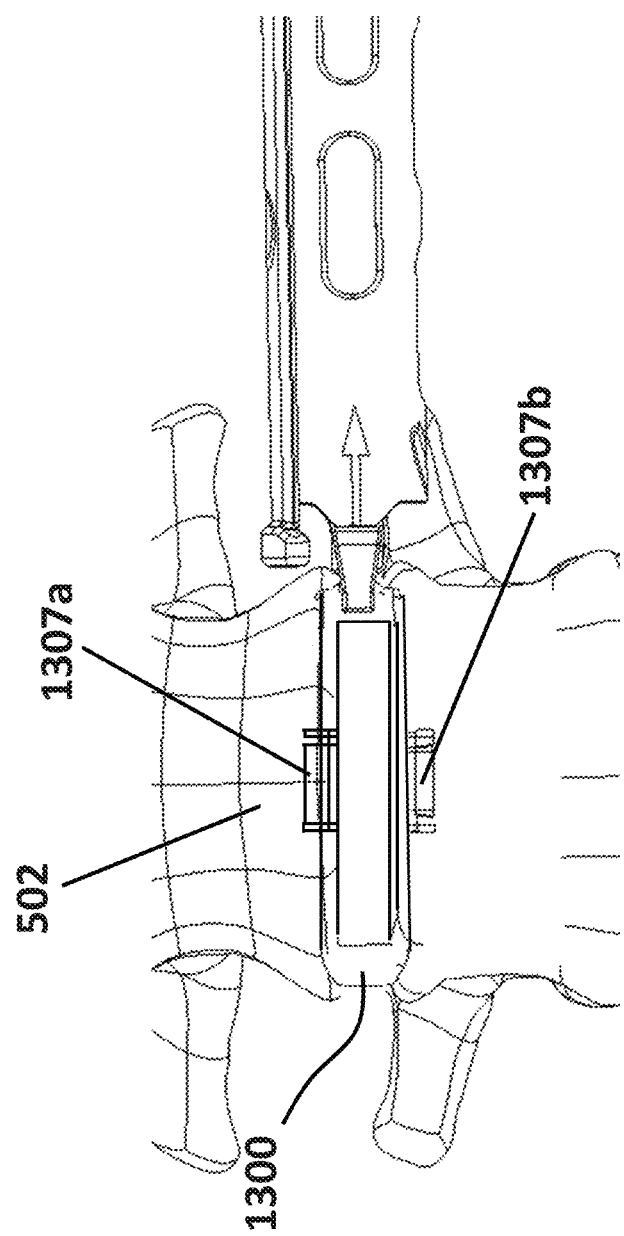

INSERTION TOOL FOR IMPLANT AND METHODS OF USE

CROSS-REFERENCE TO RELATED APPLICATION

This application claims priority to U.S. Ser. No. 62/240,447, filed Oct. 12, 2015, the disclosure of which is incorporated herein in its entirety by reference.

FIELD OF THE INVENTION

The present invention generally relates to lumbar interbody fusions, and particularly to methods and systems for guiding and delivering implants into the spine.

BACKGROUND OF THE INVENTION

Anterior lumbar interbody fusion (ALIF) is a type of spinal fusion that utilizes an anterior (front—through the abdominal region) approach to fuse the lumbar spine bones together. The intervertebral disc is removed and replaced with a spacer. The anterior technique is often used when multiple spinal levels are being fused and multiple discs need to be removed. ALIF may be performed in conjunction with or without a posterior decompression (laminectomy) and/or instrumentation (use of metal crews/rods). The anterior approach is also used when only one spinal level is fused and a posterior decompression and/or instrumentation are not required. Although the anterior lumbar approach involves retracting (moving out of the way, temporarily) large blood vessels (aorta, vena cava) and the intestines, there is a wide exposure of the intervertebral disc without retraction of the spinal nerves and neurologic structures (and therefore, a decreased risk of neurologic injury).

Alternatively, in lateral lumbar interbody fusion (lateral LIF), the surgeon makes an incision over the patient's flank. With this approach, the surgeon can reach the vertebrae and intervertebral disks without moving nerves, blood vessels, or intestines.

There is a need for improved methods and tools for inserting and fixing an implant in a desired site within a patient's spine.

There is a further need for tools that are easy to use that can both insert an implant within a desired site and deploy the implant to fix it between the adjacent vertebral bodies, when needed.

There is a further need for a tool that can remove the implant cage without breaking the cage, if needed.

An object of the invention is to provide improved methods and tools for inserting and fixing an implant in a desired site within a patient's spine.

It is a further object of the invention to provide tools that are easy for a surgeon use, and which can insert an implant cage within a desired site and deploy the cage to fix it between the adjacent vertebral bodies.

It is a further object of the invention to provide a tool that can remove the implant cage without breaking the cage, if desired.

SUMMARY OF THE INVENTION

An easy-to-use, multi-component system for insertion of an intervertebral implant and methods of use thereof are described herein. The system includes an inserter, one or more jaws for securing an implant to the system, one or more rams, and optionally, an adjustable stop. Additional components for insertion and/or removal of the implant may be included.

The inserter has a hollow body, which is configured for the insertion and removal of various components of the system, as needed. Preferably, the jaw has one or more prongs for attaching to and/or securing the implant.

The system can be assembled by inserting the proximal end of a jaw into the distal end of the inserter. Once inside the inserter, the jaw is attached to the inside of the inserter in a manner that allows axial advancement of the jaw along the inserter, such as by contacting a threaded distal end of the jaw with corresponding threads on the inside surface of the inserter body. The jaw is rotationally fixed within the inserter tube to permit tightening and implant control. The ram is inserted through the jaw and inserter body. For example, in some embodiments, the ram is inserted through the proximal end of the jaw until the distal end of the ram protrudes at the distal end of the inserter assembly. Alternatively, the ram may be inserted in the opposite end of the inserter and jaw, i.e. through the distal end of the jaw until the proximal end of the ram protrudes at the proximal end of the inserter assembly.

An adjustable stop can be attached onto the superior portion of the outer surface of the inserter body. The adjustable stop is attached in a manner that allows for rapid, tool free control over the depth of insertion of an implant in a patient's spine.

After assembly of the insertion assembly, an implant of appropriate size for the site in need of treatment in the patient's spine is introduced into the jaw such that it is secured to the jaw. Following insertion into the site in need of treatment in the patient's spine, the implant/inserter assembly can be impacted into the site between the adjacent vertebral bodies until the adjustable stop contacts the anterior edge of one of the vertebral bodies. Preferably, the implant contains one or more deployable blades in the implant, which are then deployed by means of impaction so that the implant is fixed in the inferior and/or superior vertebral bodies.

If needed, additional components are provided for safe removal of the implant.

BRIEF DESCRIPTION OF THE DRAWINGS

FIG. 4A shows an exploded view of the socket driver. FIG. 4B shows a perspective view of a cover plate inserter. FIG. 4C is a magnified view of the distal end of the socket driver, showing the head of the socket driver.

FIG. 9 shows a partial plan view of the superior portion of an exemplary inserter, featuring marked settings for selecting a desired depth of insertion of the implant relative to the outer surface of one of the vertebral bodies.

FIG. 10A shows a perspective view of an exemplary jaw for an inserter assembly. FIG. 10B shows a perspective view of the jaw of FIG. 10A in an exemplary inserter.

FIG. 13A shows a perspective view of an exemplary ram for an inserter assembly. FIG. 13B shows a perspective view of the ram of FIG. 13A inserted into an exemplary inserter assembly.

FIG. 14A shows a perspective view of an exemplary threaded rod for an inserter assembly. FIG. 14B shows a perspective view of the threaded rod of FIG. 14A inserted into an exemplary inserter assembly.

FIG. 17A shows a perspective view of an exemplary implant impaction cap for an inserter assembly. FIG. 17B shows a perspective view of the implant impaction cap of FIG. 17A inserted into an exemplary inserter.

FIGS. 18A and 18B show perspective views of an exemplary ball driver. FIG. 18B is a magnified partial perspective view of the ball driver illustrated in FIG. 18A.

FIGS. 21A and 21B show elevation (FIG. 21A) and partial perspective cross-sectional views (FIG. 21B) of an exemplary ram impaction cap attached to an inserter.

FIG. 22 shows a side view of an exemplary lateral implant fully inserted into the vertebral body with both blades deployed.

DETAILED DESCRIPTION OF THE INVENTION

I. Insertion System

The insertion system (1050, 1500) contains an inserter, a jaw, a ram and optionally, an adjustable stop. Additional components may be attached to one or more parts of the insertion system, as needed.

The inserter is configured to receive the jaw, ram and adjustable stop, each of which are removable from the inserter.

A. Inserter

Figure 1:
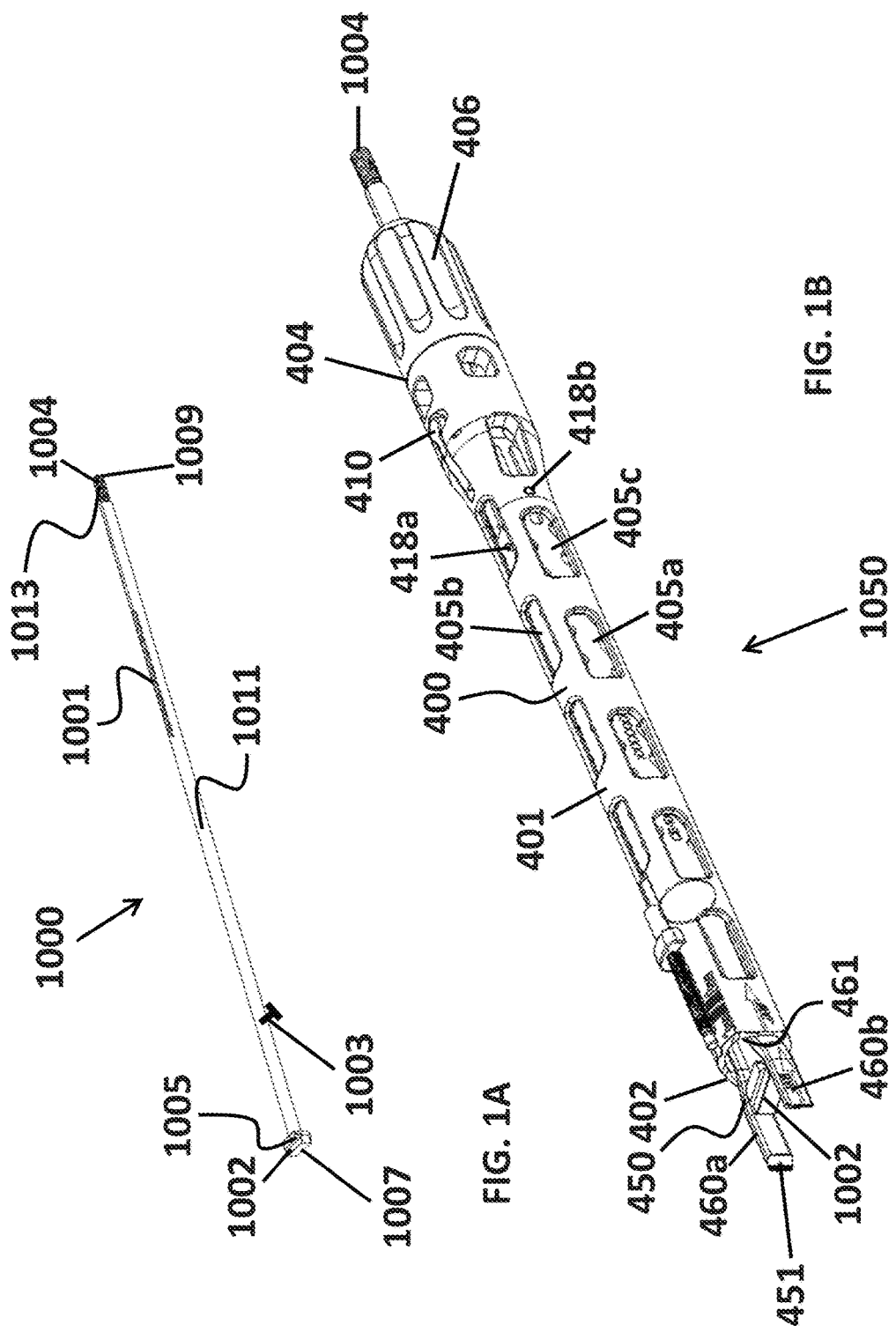
FIG. 1A shows a perspective view of an exemplary ram.
FIG. 1B shows a perspective view of an exemplary inserter assembly, with a ram inserted into a jaw inside an inserter.
Figure 7:
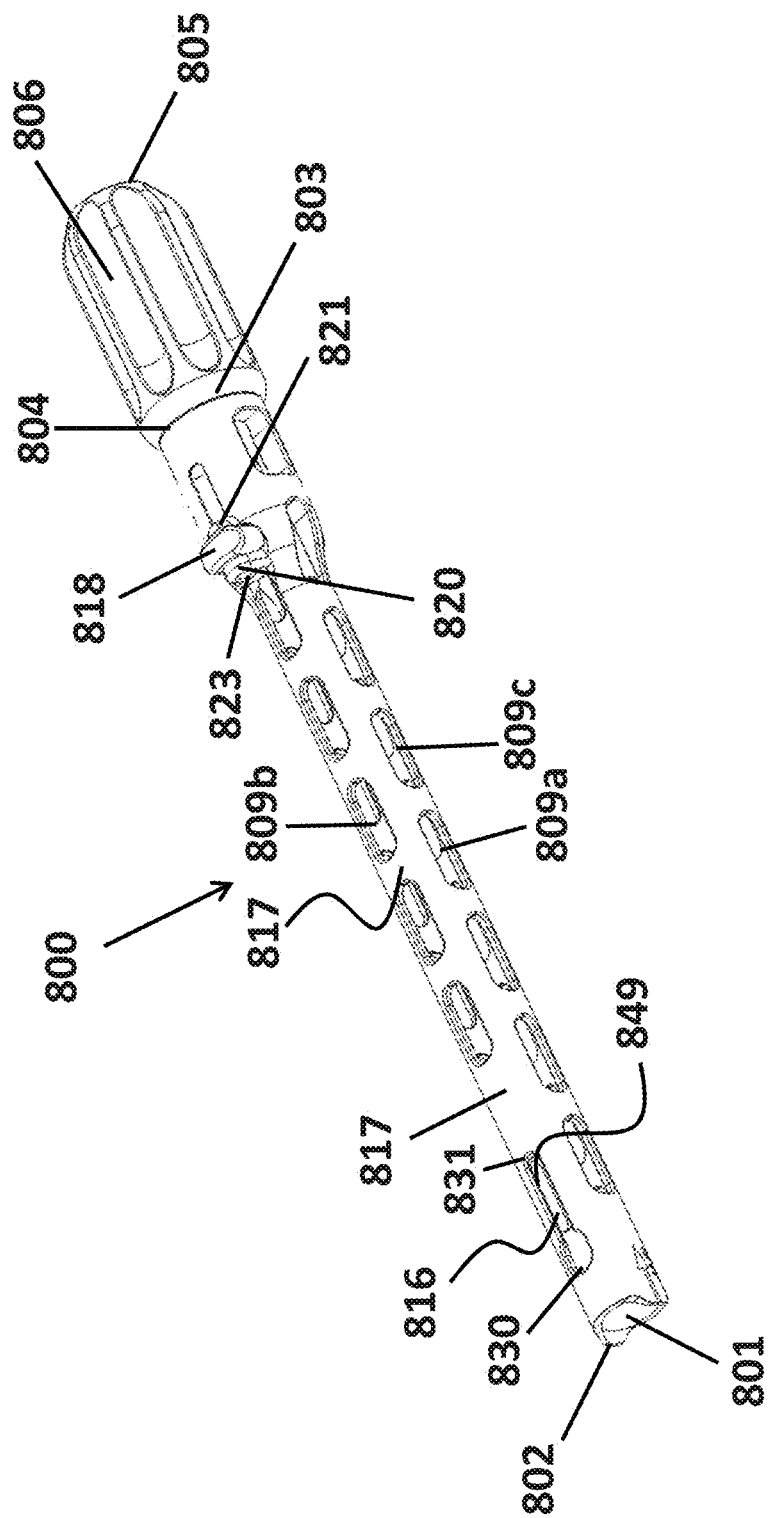
FIG. 7 shows a perspective view of an exemplary inserter.
Figure 8A:
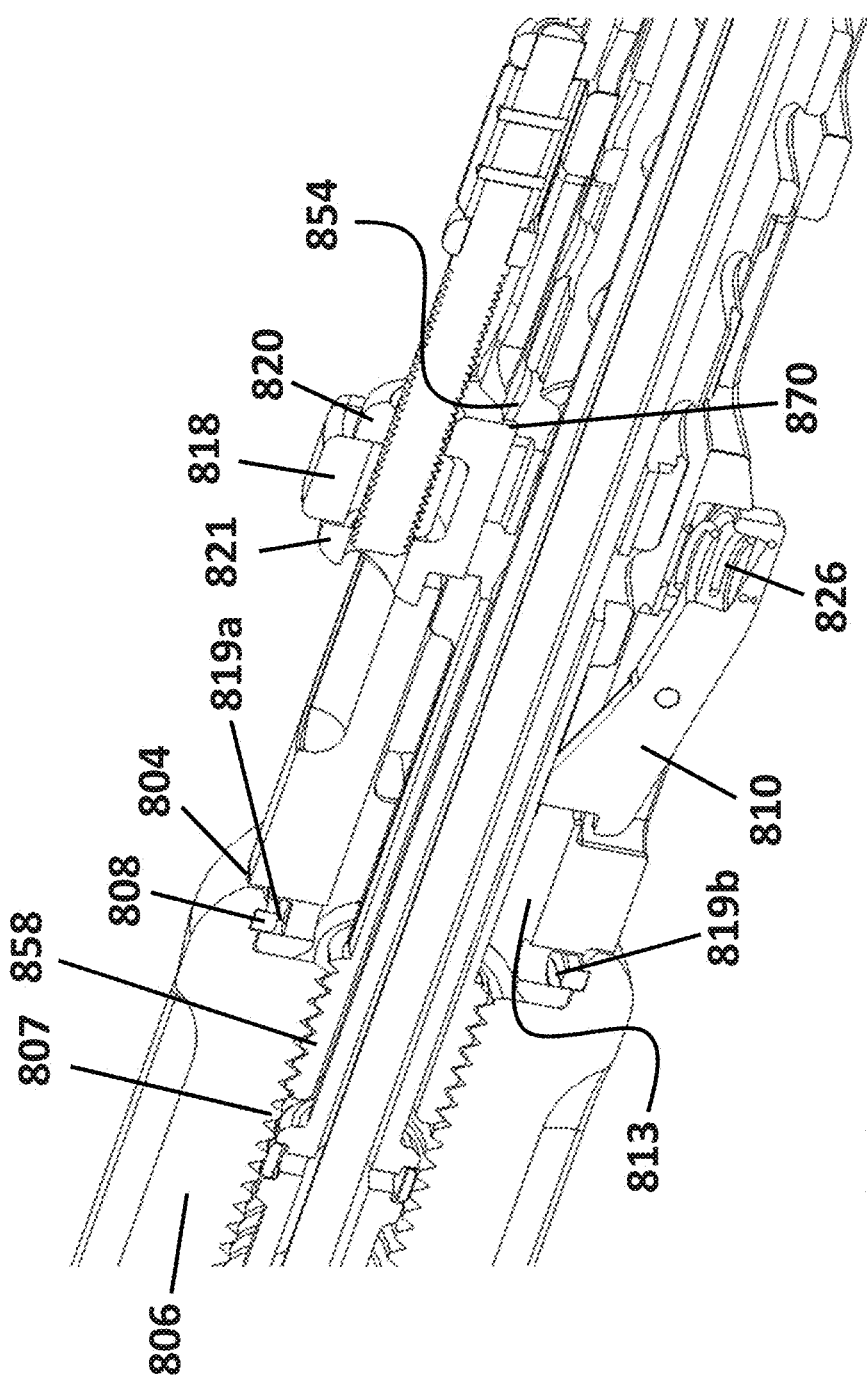
FIG. 8A shows a partial cross-sectional perspective view of an exemplary inserter assembly.

Exemplary inserters (400, 800) suitable for anterior and/or lateral insertion are illustrated in FIGS. 1B and 7. The inserter has a body (401, 817) with a hollow central cavity (403, 801) running along a central axis. The body has a superior surface (817), a distal end (402, 802) and a proximal end (404, 804), with a knob (406, 806) that is attached to the proximal end (404, 804) of the inserter in a manner that allows for free rotation of the knob. The knob may be attached to the proximal end (404, 804) by any suitable means, such as for example by a pin connection of the knob (406) to the proximal end (404) of the inserter. Alternatively, the knob may be attached to the proximal end of the inserter using a connection ring (808) as can be seen in FIG. 8A. In a preferred embodiment, two or more cleanout holes (819a, 819b) are provided at this connection (FIG. 8A). The knob (406) typically contains a plurality of threads, configured to mate with corresponding threads on a jaw.

The inserter body contains one or more, typically a plurality of openings (405a, 405b, 405c, 809a, 809b, 809c, etc.) along the length of the body. The openings allow for ease of viewing the presence and alignment of the various components or parts thereof that are inserted into the inserter. The openings may also reduce the weight and facilitate cleaning of the inserter.

Figure 8C:
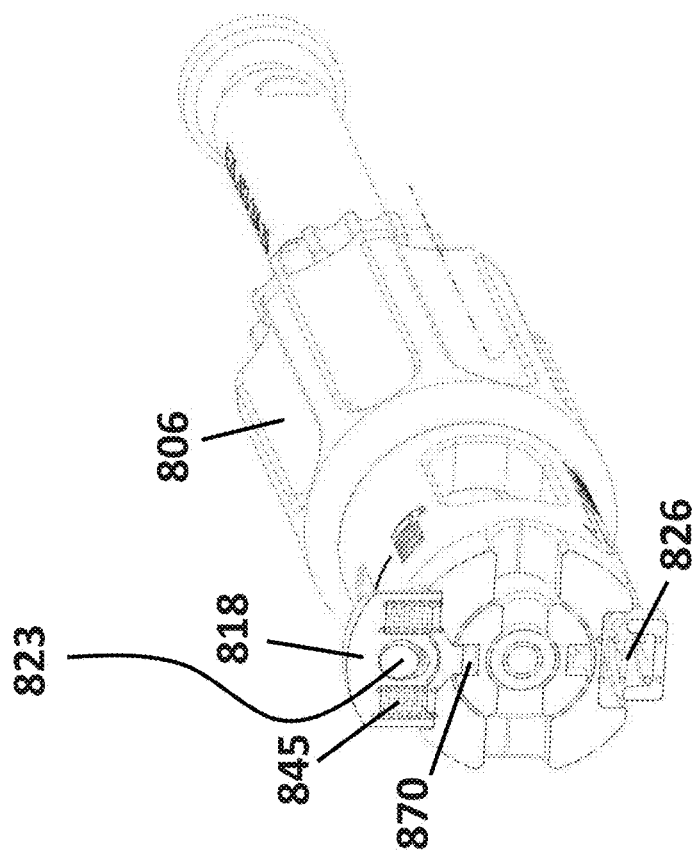
FIGS. 8B and 8C show cross-sectional perspective views of the proximal end of an exemplary inserter assembly, featuring the spring-loaded button released (FIG. 8B) and depressed (FIG. 8C).
Figure 8B:
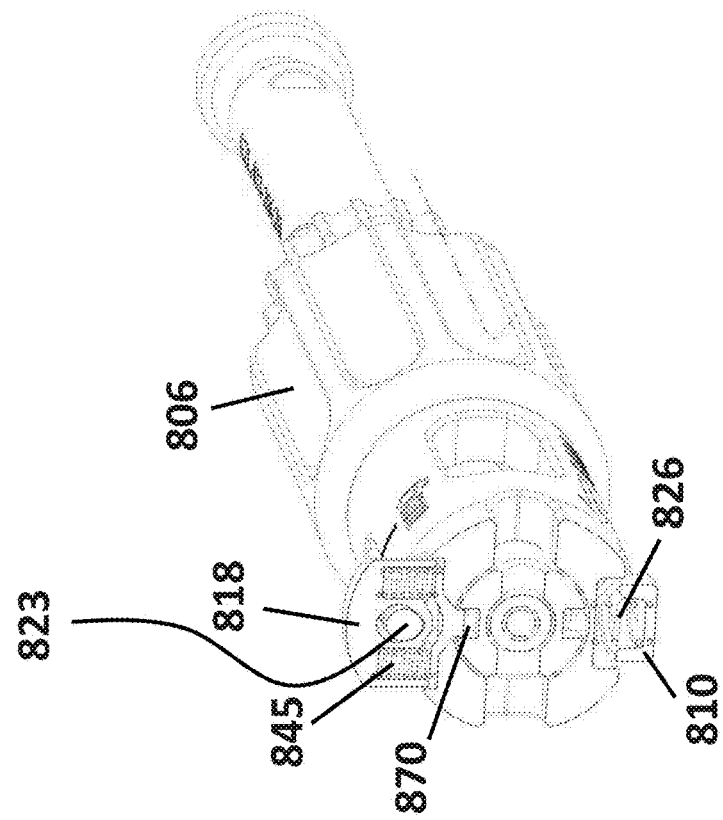
Figure 12:
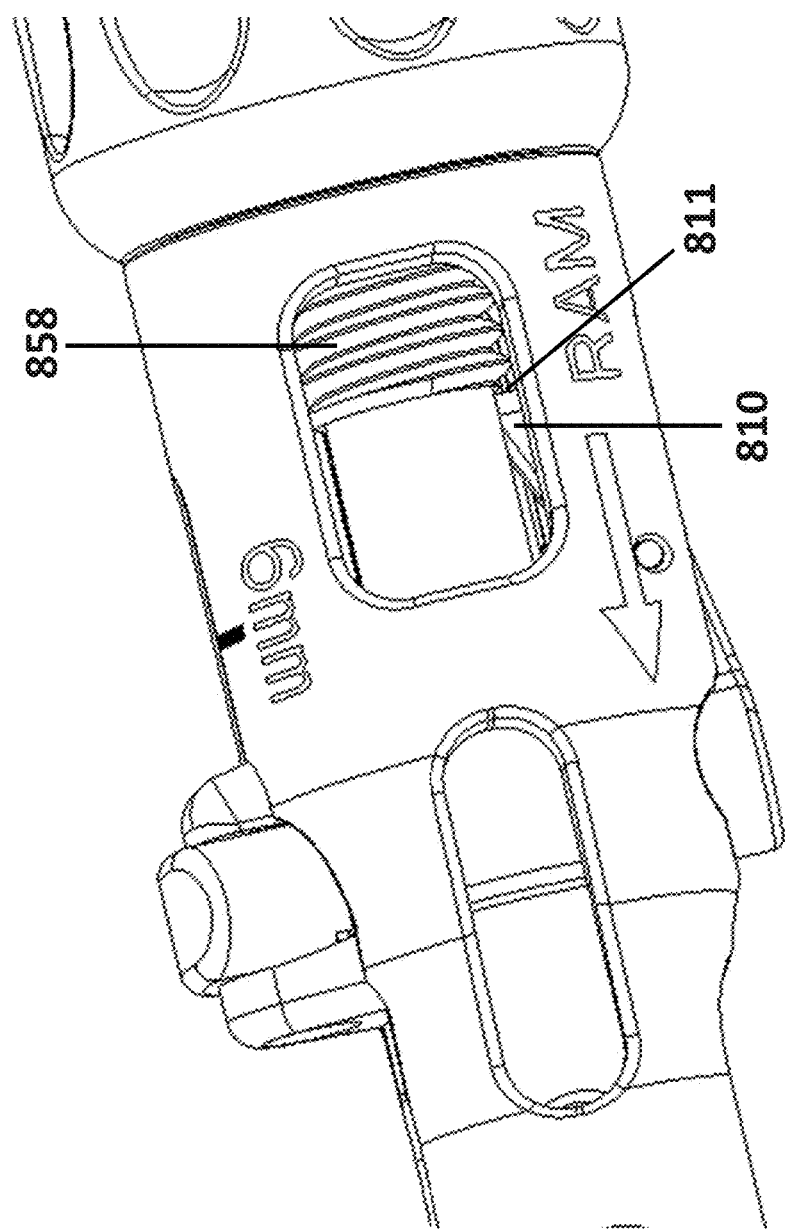
FIG. 12 shows a side view of the partial image depicted in FIG. 11, featuring the inserted jaw and spring-loaded safety pawl.

The inserter has an inferiorly located safety pawl (810), that is held in place by a pivot pin and biased by a spring (826) (FIGS. 8A-8C). As the jaw is advanced inside the inserter towards the proximal end of the inserter, the jaw passes the proximal tip (811) of the spring-loaded safety pawl (810) (FIG. 12). The proximal end (811) of the safety pawl may lock behind the threaded end (858) of the jaw inside an open area (813) in the inserter.

In some embodiments, a spring-loaded safety pawl (410) may be located on a superior surface of the inserter adjacent to the proximal end (404) of the inserter (FIG. 1B) and it generally aligns in the plane of the superior surface of the inserter. In a preferred embodiment, the inserter also has a thread on the interior surface of the proximal end of the hollow body, which is configured to mate with a corresponding thread on the proximal end of the exterior surface of the jaw when the jaw is fully inserted into the inserter and rotated relative to the inserter. In some embodiments, this thread is a male thread. In other embodiments, the thread is a female thread. In some embodiments, the inserter also has one or more lateral pins (418a, 418b) (FIG. 1B), which engage lateral slots in the jaw (not shown). Preferably, the pins are removable.

Figure 2:
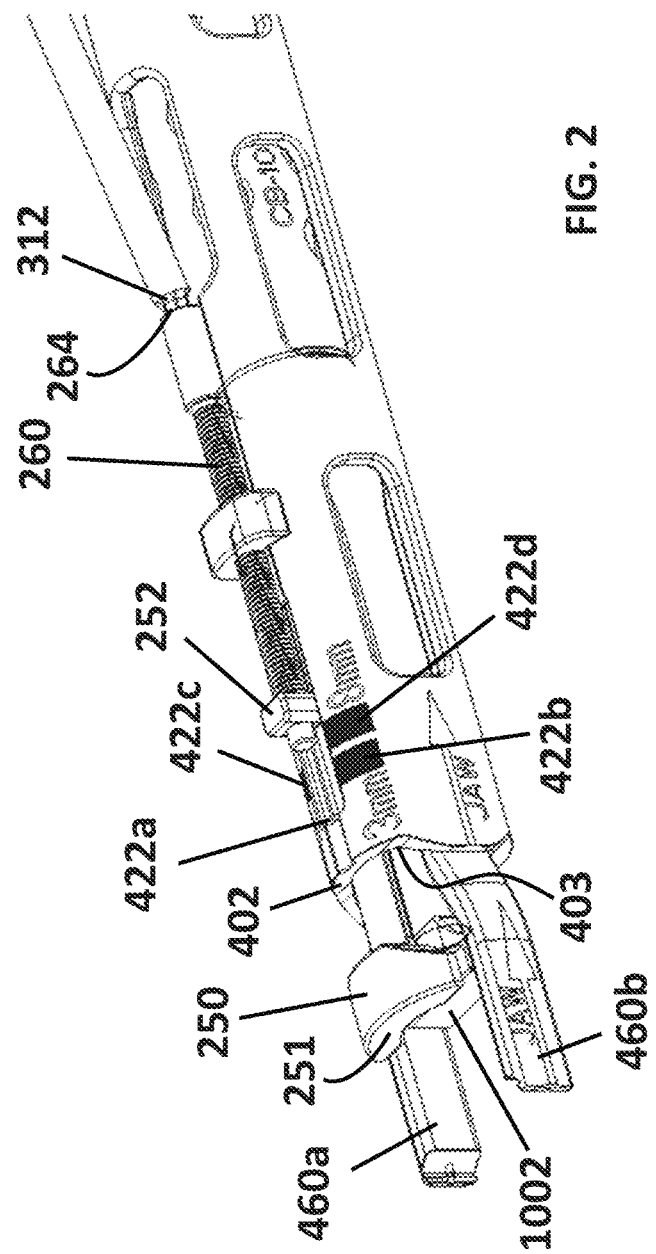
FIG. 2 shows a partial perspective view of the distal end of an exemplary inserter assembly.

In some embodiments, the superior surface of the inserter has one or more, preferably a plurality of marked settings, such as for example two, three, four, five, or more marked settings, (422b, 822b; 422c, 822c; and 422d, 822d), that correspond with insertion depths for an implant. Optionally, settings may include one unmarked setting (422a, 822a), which typically corresponds with the "zero" setting, such as shown in FIGS. 2 and 9. Typically, at least one setting and preferably more than one setting is marked, such as with a measurement or other indicator (e.g. color, number, letter, etc.) to distinguish the different settings. Typically the markings correspond with the distance between the anterior wall of the implant measured from the anterior end of the adjacent vertebral body in contact with the distal end of the adjustable stop.

In another embodiment, the superior portion (817) of the inserter has a keyhole slot (816) located towards its distal end (802) and a protruding spring-loaded button (818) located towards the proximal end (804) (FIG. 7). The keyhole slot (816) has a distal end (830) and a proximal end (831). In some embodiments, the distal end (830) of the keyhole slot (816) is wider than the proximal end (831). The keyhole slot is usable in conjunction with the key tab (1158) of an optional adjustable stop.

Figure 11:
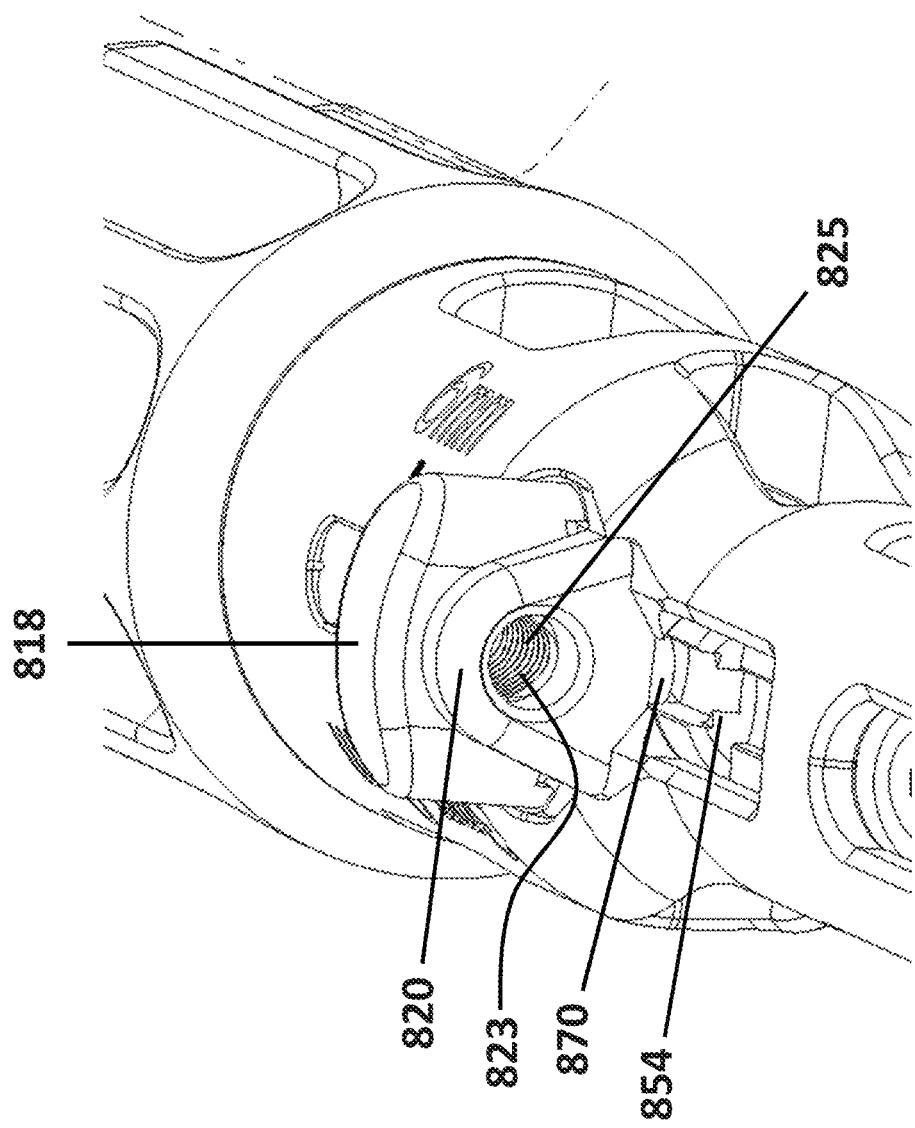
FIG. 11 shows a partial perspective view of the superior portion of an exemplary inserter assembly, which includes a protruding spring-loaded button and a channel therethrough for receiving a threaded portion of an adjustable stop.

The button (818), which is biased outwardly by a spring (845) (FIGS. 8B and 8C), has a distal end (820), a proximal end (821), and a channel (823) extending from its distal end to its proximal end (FIGS. 7 and 11). The button is usable in conjunction with an optional adjustable stop. Depressing the button (818) on the inserter, allows the adjustable stop to be advanced axially along the inserter until it reaches a desired position, such as 0 mm (located at the unmarked setting 822*a*), 3 mm (822*b*), 6 mm (822*c*), or 9 mm (822*d*) (FIG. 9). The adjustable stop locks in position upon release of the button. FIGS. 8B and 8C illustrate exemplary inserter assemblies with the button (818) released and depressed, respectively.

Preferably, the surface beneath the button is curved, forming a channel (823) (FIG. 11). In some embodiments, the curved surface of the channel contains a plurality of grooves or threads. Preferably, the lower portion of the curved surface contains a plurality of grooves or threads (825), configured to engage a corresponding thread, such as for example the thread (1166) of an adjustment rod (1156) (FIG. 15A), while the upper portion of the curved surface of the channel is smooth. The adjustable stop has a suitable size and shape to fit in the channel (823) in the button and the keyhole slot (816) on the inserter. The key tab (1158) on the inferior surface (1162) of the adjustable stop is insertable into the distal end (830) of the keyhole slot (816) of the inserter. In some embodiments, translational movement of the adjustable stop towards the proximal end of the inserter traps the head (1163) of the key tab on the inferior portion (849) of the proximal end (831) of the keyhole slot and locks the adjustable stop in place with respect to the inserter.

B. Jaw

A jaw (450, 850) configured to receive and hold an implant having a particular width is insertable into the inserter and removable therefrom, typically via the inserter's distal end (402, 802) (FIGS. 1B, 10A and 10B). The jaw has a hollow shaft (461, 856) with a distal end (451, 851) and a proximal end (853). The jaw can be divided into three sections: a first section (857) configured to receive and hold an implant, which is located at the distal end of the jaw; a second section (859) located at the proximal end which is configured to attach to an interior surface of the inserter body; and a third section (861) located between the first and second sections which has a suitable size and shape to fit inside the inserter body. The first section (857) typically has one or more prongs (460*a*, 460*b*, 860*a*, 860*b*), which are configured to hold an implant. The second section (859) is typically hollow and connects with the third section (861), which is generally in the shape of a hollow shaft (856) (FIG. 10A). In some embodiments, the third section also contains a superiorly located depression or pocket (854) adjacent to the proximal end (FIG. 10A).

When the jaw is fully inserted in the inserter, the second and third sections are inside the inserter, but at least a portion of the first section, including the distal end of the jaw (451, 851) and the one or more prongs (460*a*, 460*b*, 860*a*, 860*b*) of the jaw, typically protrudes beyond the distal end of the inserter.

The second section of the jaw also includes an attachment portion, such as a thread (858) or other features configured to attach to the inserter knob (806), which is located on the proximal end of the exterior surface of the second section of the jaw (FIG. 10A). In some embodiments, the thread is male. In other embodiments, the thread is female. In some embodiments, the thread on the jaw is configured to mate with the thread on the interior surface of the knob (806). In other embodiments, the thread on the jaw (858) mates with threads (807) present on the interior of the knob (806) (FIG. 8A). One of skill in the art would understand that the thread as a means of attachment is merely illustrative, and that alternative means of attachment, such as friction fit or a structure with grooves that lock in place when turned, may be used.

In some embodiments, the jaw has lateral slots, as well as a superiorly located slot. In other embodiments, the jaw has a superiorly located slot (854) as well as a series of superior, inferior, and bilateral holes (855*a*, 855*b*, 855*c*, etc.) (FIG. 10A). The holes may reduce the weight and provide ease of cleaning of the inserter. The superiorly located slot (854) is configured to engage the key and slot feature (870) of the inserter (FIG. 11), as explained below.

In some embodiments, the distal tip of the spring-loaded pawl (410) of the inserter can engage a groove in the threaded portion of the jaw when it is initially inserted into the inserter. Then the proximal end of the spring-loaded pawl can be depressed to raise the distal tip of the pawl so that it is not in contact with the thread, allowing complete insertion of the proximal end of the jaw into the inserter (FIG. 1B). In other embodiments, jaw rotation is controlled by the key and slot feature (870) of the inserter, by fitting the key and slot feature (870) into the slot (854) of the jaw (FIG. 11). Optionally, an audible sound, such as one or more clicks, may be heard as the threaded end (858) of the jaw passes by the proximal tip (811) of the spring-loaded safety pawl (810) (FIG. 12).

In a preferred embodiment, the jaw contains two or more prongs (460*a*, 460*b*, 860*a*, 860*b*) or other structures for receiving and securing an implant to the jaw, located at its distal end (451, 851). The prongs can be configured to hold a cage of a particular size. In some embodiments, the prongs can hold a cage that ranges in size from about 20 mm in length to about 35 mm in length and from about 25 mm in width to about 40 mm in width. For example, the jaw can have a sufficient width between the prongs to hold an implant that is 23 mm×28 mm in size, 26 mm×32 mm in size, or 32 mm×38 mm in size. In other embodiments, the prongs can hold a cage that ranges in width from about 15 mm to about 30 mm. One of ordinary skill in the art would understand that the prongs can be easily modified to receive spinal implants having other dimensions. Preferably, a single jaw is able to receive and mate with a variety of different sized cages.

C. Ram

A ram (1000, 1100) configured to fit into the hollow shaft of the jaw (third section of the jaw) and between the prongs of a jaw is also provided herein (FIGS. 1A and 13A). The ram can have any suitable shape, but is typically in the shape of a long, straight, hollow bar.

The ram has a distal end (1007, 1103) and a proximal end (1009, 1105). The ram can be divided into three sections: a first section (1005, 1101) configured to fit between the prongs of the jaw, correct the orientation of the jaw, and/or prevent rotation of the jaw, which is located at the distal end of the ram; a second section (1013, 1109) located at the proximal end which typically contains a threaded end configured to attach to other components, such as an implant impaction cap (1200) or a ram impaction cap (1305) with corresponding threads that mate thereto or other connector(s); and a third section (1011, 1107) located between the first and second sections which has a suitable size and shape to fit inside the third section of the jaw. When the ram is completely inserted into the inserter and jaw, the distal end (1103) is generally aligned with the distal end of the jaw (851) and the two prongs of the jaw and protrudes beyond the distal end (802) of the inserter. In some embodiments, the distal end of the first section (1005) of the ram has a head (1002), which is configured to engage the strike plates of an implant.

In some embodiments, the ram may be rotationally stabilized to the jaw with a lateral pin (1003), as shown in FIG. 1A. The pin, which slides in an internal slot in the jaw, fits into a hole in the ram, and prevents ram misalignment that could interfere with the face of the implant and misalign with the implant actuation mechanism. In some embodiments, the ram has a superiorly located tooth pattern (1001). In these embodiments, the distal tip of the spring-loaded pawl (410) of the inserter is configured to engage one tooth at a time, allowing for the ram to be moved in a controlled manner forward or backward relative to the inserter to a desired location. In other embodiments, the ram has an anti-rotation device (1102) in the first section (1101), allowing for correct orientation in relation to the jaw (FIGS. 13A and 13B). The anti-rotation device is generally configured with at least two (1111a, 1111b, etc.) that can align with corresponding surfaces on the interior of the first portion of the jaw (FIG. 13A). In some embodiments, the surfaces (1111a, 1111b, etc.) are flat. Preferably, surface (1111a) is curved.

In some embodiments, the ram has a threaded portion (1104) at its proximal end (1105) (FIG. 13A) and a rim (1131) located distally to the threaded portion. The rim (1131) may produce friction between the ram and the jaw when the ram is inserted in the jaw, thus retaining the ram in position.

D. Adjustable Stop

Figure 15A:
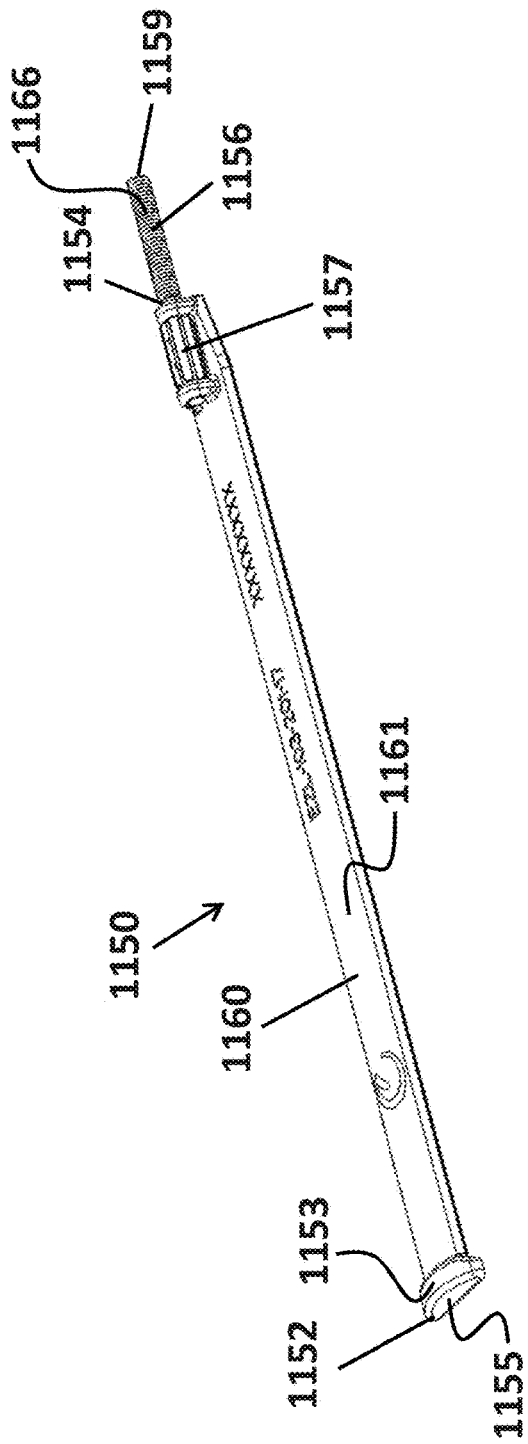
FIG. 15A shows a perspective view of an exemplary adjustable stop for an inserter assembly.
Figure 15B:
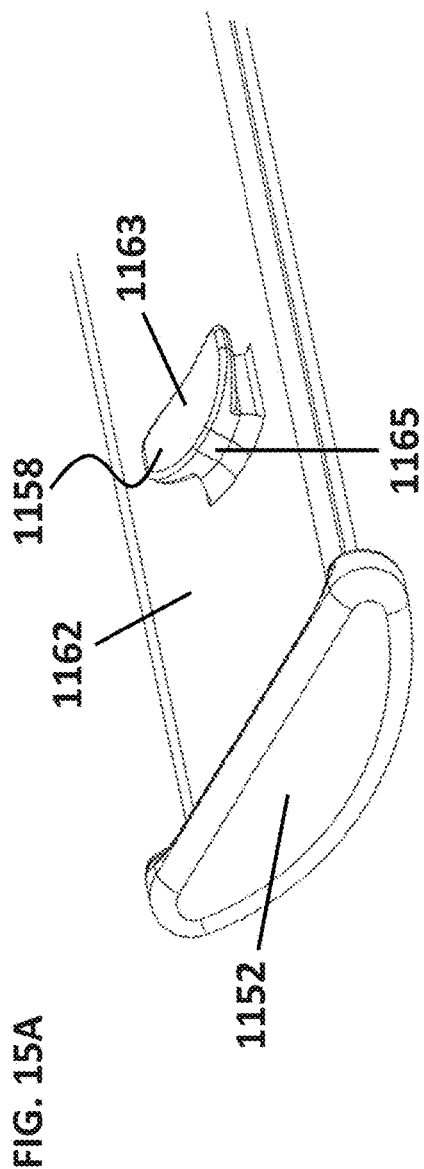
FIG. 15B shows a partial perspective view of the distal end of the adjustable stop of FIG. 15A, featuring the key tab.

Optionally, an adjustable stop (250, 1150) is provided (FIGS. 2, 15A, and 15B). In some embodiments, the adjustable stop contains a thin, long body (1161) with a curvature that corresponds to the superior surface of the inserter. The body (1161) terminates at its distal end (1152, 251) with a stop portion (1153) that is wider and taller than the body. The body (1161) contains a proximal end (1154), a distal end (1152), a superior surface (1160), and an inferior surface (1162). The stop portion has a substantially flat distal surface (1155), which is configured to abut the anterior surface of a vertebral body during insertion of the implant (FIGS. 15A and 15B).

In some embodiments, the adjustable stop is insertable into and also removable from the inserter. In other embodiments, the adjustable stop is attachable to the superior surface (or inferior surface) of the inserter and removable therefrom.

In some embodiments, when the adjustable stop (250) is inserted into the distal end of the inserter, the distal end (251) of the adjustable stop extends beyond and is adjacent to the distal end (402) of the inserter (FIG. 2). Optionally, the adjustable stop includes a superiorly located proximal lug (252). In some embodiments, the lug is configured to receive an adjustment rod (260), such as shown in FIG. 2.

Figure 16:
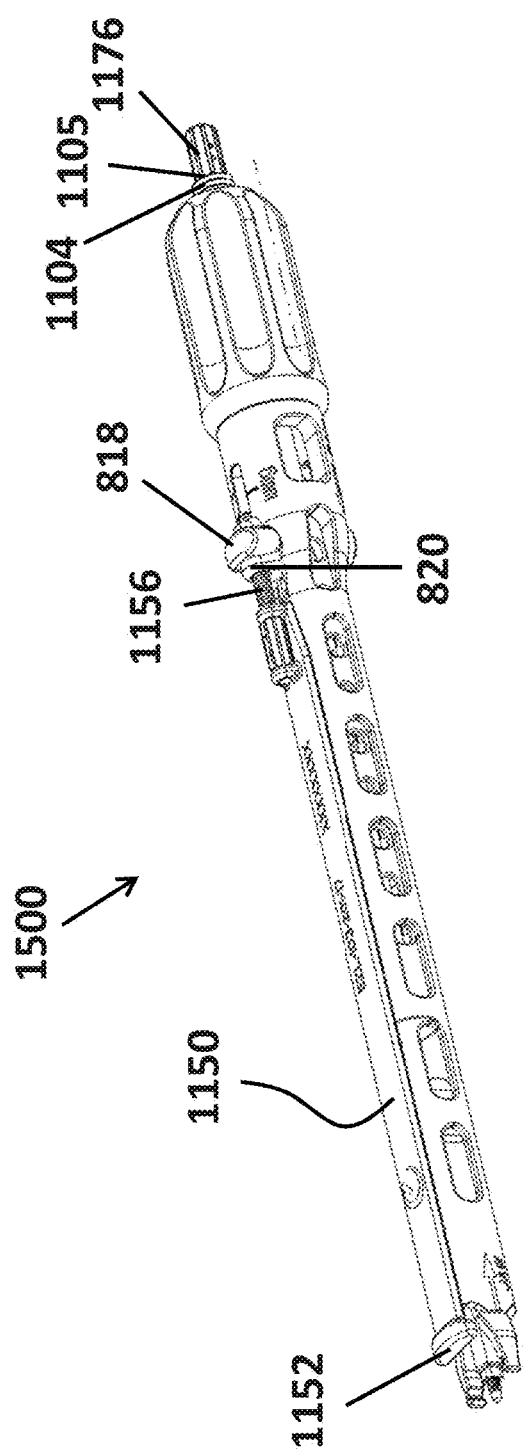
FIG. 16 shows a perspective view of a fully assembled exemplary inserter assembly.

In other embodiments, the proximal end (1154) of the adjustable stop contains a hollow adjustment wheel (1157), which is configured to receive an adjustment rod (1156). Upon insertion of the adjustment rod into the adjustment wheel, the adjustment rod becomes a portion of the adjustable stop, as illustrated in FIG. 15A. The adjustment rod (1156) is insertable at its opposite end (1159) into the distal end (820) of the spring-loaded button (818), on the superior surface of the proximal end of the inserter, as seen in FIG. 16. Depression of this button allows for positioning of the adjustable stop as well as for assembly and removal. Rotation of the adjustment wheel (1157) allows the thread (1166) of the adjustment rod (1156) to advance into the channel (823) of the button. The thread (1166) of the adjustment rod (1156) engages a corresponding thread (825) on the inferior portion of the channel (823), allowing the adjustable stop to advance toward the proximal end or the distal end of the inserter.

In some embodiments, the adjustable stop also contains a key tab (1158) located toward the distal end (1152) of the inferior side (1162) of the body, as shown in FIG. 15B. Preferably, the key tab (1158) has a wide head (1163) and a tapered neck (1165). The head (1163) of the key tab is insertable into the distal end (830) of the keyhole slot (816), allowing the neck (1165) to slide axially along the keyhole slot towards the proximal end (831) of the keyhole slot. Axial movement of the key tab toward the proximal end (831) of the keyhole slot lodges the head (1163) of the key tab on the inferior portion (849) of the proximal end (831) of the keyhole slot, locking the adjustable stop in place with respect to the inserter.

FIG. 16 shows an exemplary fully assembled inserter system, and including an adjustable stop. When fully assembled, the distal end of the adjustable stop extends beyond the distal end of the inserter, and is located between the distal end of the inserter and the distal end of the jaw and/or ram. However, the precise location of the distal end of the adjustable stop can be moved and set to ensure that the implant is inserted into the desired location or depth between the adjacent vertebral bodies.

Threaded Rod

Generally, an adjustment rod (260, 1156) is provided to facilitate various settings for the adjustable stop (FIGS. 2 and 15A). In some embodiments, the adjustable stop can be adjusted to 0 mm measured relative to the anterior end of one of the vertebral bodies. In this embodiment, the insertion end of the implant is placed adjacent to the anterior end of the vertebral bodies. The adjustable stop can be adjusted to other preset measurements, such as 3 mm, 5 mm, or 8 mm (FIG. 2), or 3 mm, 6 mm, or 9 mm (FIG. 9), or intervals between these measurements. Other preset measurements may be provided on the insertion assembly. The person of ordinary skill in the art will understand that other settings can be established to ensure that the cage is properly placed within the desired site.

In one embodiment, the adjustment rod (260) has a suitable size to be insertable through a lug (252) of the adjustable stop (250). The location of the adjustable stop can be selected to ensure that the implant is placed in the proper position between two adjacent vertebrae.

E. Additional Components

1. Impaction Caps

In some embodiments, an implant impaction cap (1200) is provided (FIGS. 17A and 17B). In some embodiments, a ram impaction cap (1350) is provided (FIG. 21A). Each of the ram impaction cap and the implant impaction cap contain a large, substantially flat surface (1201, 1351) at their proximal ends (1203, 1353), which optionally has a larger surface area than the body of the ram or implant impaction cap.

Figure 17C:
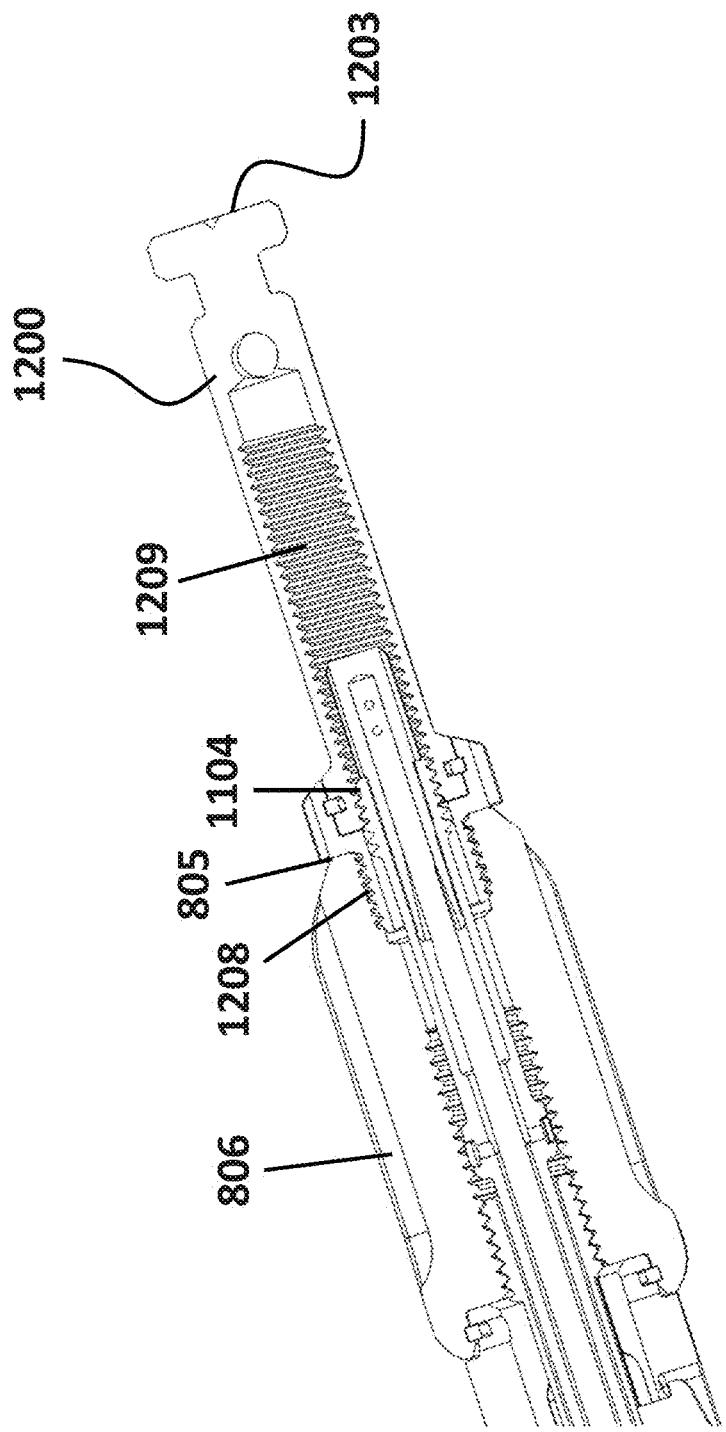
FIG. 17C shows a cross-sectional perspective view of the implant impaction cap of FIGS. 17A and 17B inserted into an exemplary inserter.

In some embodiments, the implant impaction cap threads onto the proximal end (1004) of the ram (1000) and the internal thread of the knob. In other embodiments, the implant impaction cap (1200) threads onto the threaded portion (1104) of the ram (1100) via an internal thread (1209) (FIG. 17C). Alternatively, the implant impaction cap (1200) threads into the proximal end (805) of the knob (806)

via its distal threaded portion (1208) (FIGS. 17A, 17B). The flat surface (1201) of the proximal end (1203) of the impaction cap may be impacted to push the implant into a desired site between the adjacent vertebral bodies. In some embodiments, the handle portion (1204) of the implant impaction cap may be rotated to retract the blades into the body of the implant to ensure that they clear the vertebral bodies during insertion.

In some embodiments, the ram impaction cap (1350) has a hollow shaft (1355). Preferably the shaft is threaded (1357), allowing it to thread onto or alternatively otherwise attach to the proximal end (1004, 1104) of the ram (1000, 1100) (FIG. 21B). The flat surface (1351) of the proximal end (1353) of the ram impaction cap is configured to be hit or impacted to thrust the blades (if present) in the implant into the superior and inferior vertebral bodies. For example, impaction of the ram impaction cap can deploy the blades (1307a, 1307b) of an implant, so that the blades protrude superiorly and inferiorly through the implant cage, as seen in FIG. 22. Alternatively the proximal end (1353) of the ram impaction cap can be impacted to push the implant into a desired site between the adjacent vertebral bodies. Alternatively the proximal end (1203, 1353) of the impaction caps may be configured to attach a slap hammer.

2. Threaded Rod

In some embodiments, a threaded rod (1170) is provided. The threaded rod (1170) has a proximal end (1174) and a distal end (1172). Attached to the proximal end (1174) is a bi-lobed flange (1177a, 1177b), with a thumb wheel (1176) attached to its proximal end (FIG. 14A). Adjacent to the distal end (1172) is a threaded portion (1173), which in certain embodiments is configured to engage the impact post of an implant. The threaded rod (1170) may be insertable into the ram (1100), as illustrated in FIG. 14B. When the threaded rod is inserted into the ram, the bi-lobed flange (1177a, 1177b) may bias outwardly to produce friction inside the knob, thus retaining the threaded rod in position. In some embodiments, the threaded rod may be used to deploy the blades of an implant by impacting the thumb wheel (1176) directly. The threaded rod may also provide positive alignment with respect to the ram (1100). The threaded rod is also used to maintain contact between the abutting surfaces of the implant impact post during impaction. The threaded rod also allows tensile loads to be applied to the implant impact post to permit blade retraction.

3. Ball Driver

In some embodiments, a ball driver (310) is provided to adjust the location of the adjustable stop (FIGS. 18A and 18B). The ball driver contains a distal tip (312) that is insertable into a depression or hole at the proximal end (264) of the adjustment rod (260). The distal tip of the ball driver (310) preferably has a shape that is configured to mate with the shape of the depression or hole at the proximal end of the adjustment rod (260). By rotating the ball driver in one direction, the threaded rod rotates and advances along the inserter, pushing the adjustable stop away from the distal end of the inserter. Rotating the ball driver in the opposite direction moves the treaded rod in the opposite direction, i.e. pulls the adjustable stop towards the distal end of the inserter (FIG. 2).

In some embodiments, the ball driver (310) may be used to secure the implant in its deployed position. In some embodiments, the ball driver (310) has a distal tip (310) in the shape of a hexalobe (FIGS. 18A and 18B).

4. Cover Plate Inserter

Figure 4:
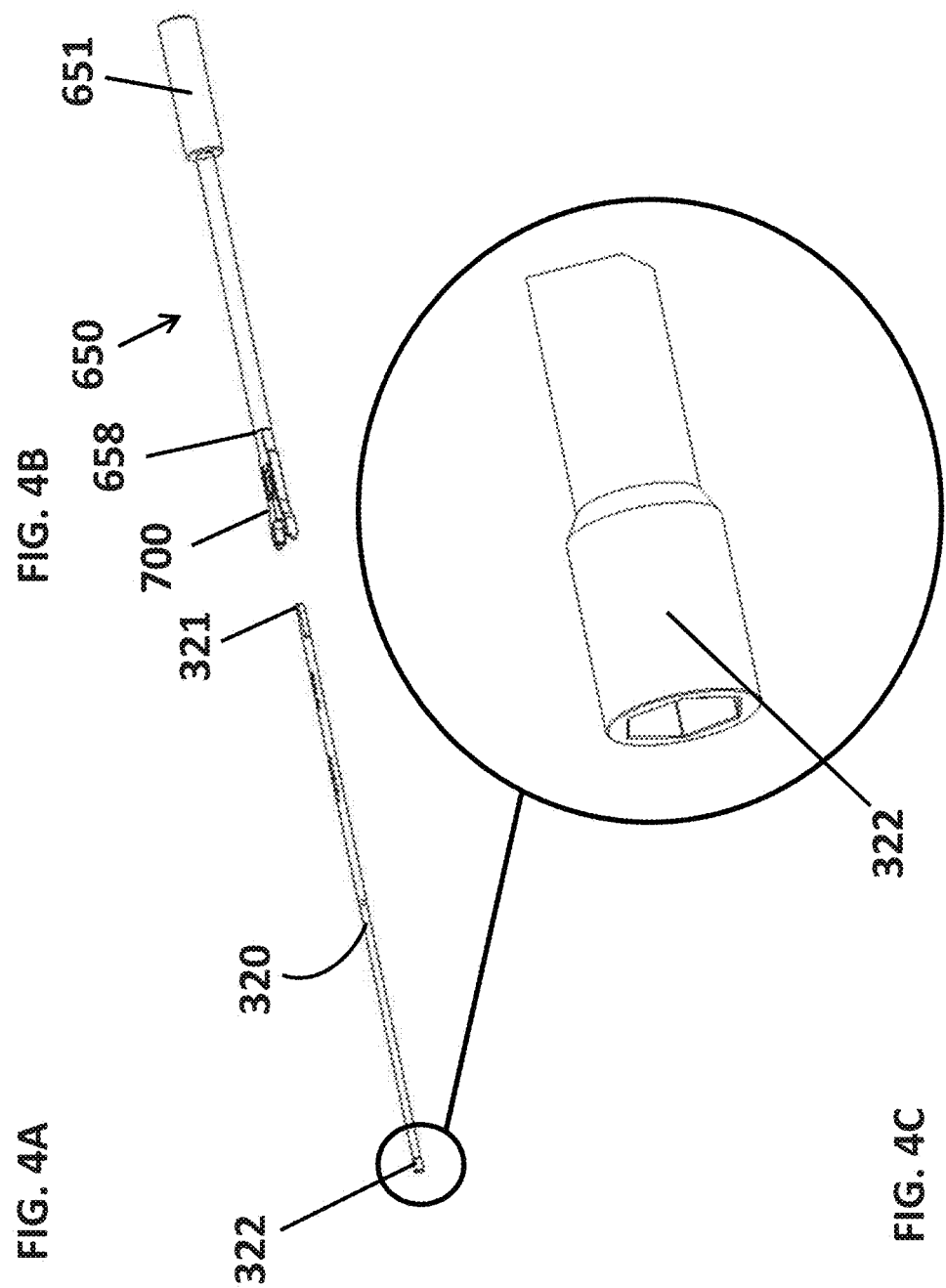
FIGS. 4A-4C show views of an exemplary cover plate inserter assembly in various stages of assembly.

In some embodiments, a cover plate inserter (650) is provided (FIG. 4B). Preferably, the cover plate inserter is hollow, with a slot or opening located at its proximal end.

Preferably, a cover plate inserter tip (700), which is threadable onto the distal end (658) of the cover plate inserter is also provided (FIG. 4B). The cover plate inserter tip may be sized to hold a cover plate suitable for a particular size of implant cage. In some embodiments, the cover plate inserter tip is able to hold a cover plate having a suitable size to cover the anterior end of an implant cage that ranges in size from about 20 mm in length to about 35 mm in length and from about 25 mm in width to about 40 mm in width. For example, the cover plate may have a sufficient size to cover an end, typically the anterior end, of an implant that is 23 mm×28 mm in size, 26 mm×32 mm in size, or 32 mm×38 mm in size. One of ordinary skill in the art would understand that the cover plate inserter tip can be easily modified to hold a cover plate having other dimensions.

In some embodiments, a socket driver (320) is provided (FIGS. 4A and 4C). The proximal end (321) of the socket driver can slide into the distal end of the cover plate inserter tip (700) and inserter (650). A driver handle (651) can be affixed to the proximal end (321) of the socket driver.

5. Removal Tools

In some embodiments, a removal tool (950) is provided. Preferably, the removal tool includes a slap hammer attachment located at its proximal end.

Figure 6:
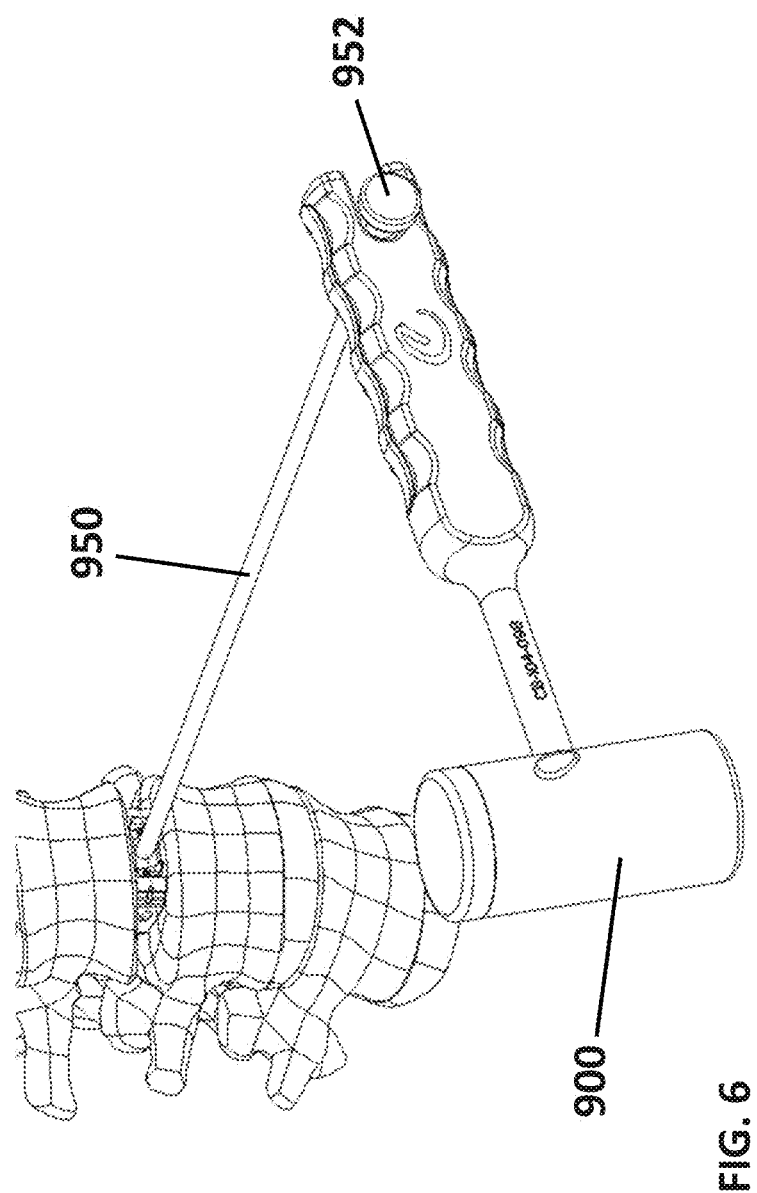
FIG. 6 shows a perspective view of an exemplary anterior implant removal tool assembly.

Optionally, a mallet (900) is provided, as shown in FIG. 6. In alternative embodiments, a tuning fork or a "slap hammer" for removal is provided.

II. Kit

The inserter may be provided as part of a kit for one or more spinal implants, such as an ALIF or a lateral LIF. The kit may contain an inserter, at least one jaw, a ram, and optionally, an adjustable stop, as described above. The kit may also contain an implant and an implant cover plate. Optionally, the kit contains a plurality of different sized implants. Optionally the kit also contains a plurality of different sized cover plates, with corresponding sizes to fit on the anterior ends of the plurality of different-sized implants.

Preferably, the kit contains a plurality of jaws of different widths to allow for use with implants of different widths, or with a single jaw that fits all widths of implants. Exemplary implant insertion systems that can be assembled from components in a kit is illustrated in FIGS. 1B and 16.

The kit may also contain an implant impaction cap and/or a ram impaction cap.

In some embodiments, the kit optionally also contains a cover plate inserter, a cover plate inserter tip, and a cover plate screw driver.

In some embodiments, the kit may also contain an implant removal tool and/or a mallet.

The kit typically contains instructions for care and/or use of the insertion system.

III. Methods of Use

A. Preparation of Inserter

A jaw (450, 850) sized for the implant to be used is inserted into the distal end (402, 802) of an inserter (400, 800) (FIGS. 1B, 10A, and 10B). Upon insertion, the jaw is rotated clockwise and in some embodiments, the proximal end of the spring-loaded pawl (410) located on the inserter is depressed, allowing the jaw to advance axially along the hollow shaft of the inserter (FIG. 1B). The jaw is inserted into the inserter until the thread on the jaw passes the threads on the interior of the inserter and reaches an open area (813) inside the inserter. Once the thread of the jaw is inside this open area, the pawl can be released. The distal tip of the pawl contacts or is directly above the depression or pocket of the jaw.

The jaw is now free to rotate inside the inserter, which also allows some axial translation of the jaw relative to the inserter. This position allows orientation and alignment of the jaw. The jaw can now be rotated and moved axially. In some embodiments, to properly align the jaw in the inserter, the jaw is rotated until one or more pins (418a, 418b) in the inserter engage lateral slots in the jaw.

In other embodiments, the jaw advances until an indicator, such as the contact of the threaded end of the jaw with a portion of the pawl indicates that the threaded end (858) of the jaw has passed the spring-loaded safety pawl (810) (FIG. 12). Optionally this contact produces an audible click or other indicator. Proper rotation may be controlled by fitting the key and slot feature (870) of the inserter into the slot (854) of the jaw (FIGS. 8A and 11).

The jaw can be pushed axially while the inserter knob (406) is turned to engage the thread of the jaw into the threads of the knob, advancing the jaw along the inserter as shown in FIGS. 1B and 10B.

In some embodiments, a ram (1000) (FIG. 1A) sized to fit in the jaw (450) is inserted through the distal end of the jaw, as shown in FIG. 1B. Preferably, the ram includes an anti-rotation device to ensure correct orientation of the jaw. A machined pocket on the jaw shaft is aligned to the pins (418a, 418b) and pressed into the jaw shaft by rotating on the proximal end (1004) of the ram, which protrudes from the proximal end of the inserter (as shown in FIG. 1B). This aligns a tooth pattern (1001) located on the ram to the pawl (410). The knob (406) of the inserter can be rotated clockwise to further draw the jaw shaft (461) towards the practitioner. The pawl drops through a pocket (not shown) in the jaw shaft and engages the tooth pattern in the ram, preventing unintentional axial movement of the ram. Further stability is optionally provided by a lateral pin (1003), which fastens the ram to the jaw (FIG. 1A).

In other embodiments, the ram (1100) (FIG. 13A) is inserted through the proximal end of the jaw, as shown in FIG. 13B. Preferably, the ram has an anti-rotation device (1102) for correct orientation of the jaw relative to the inserter. A threaded rod (1170) is advanced into the proximal end (1105) of the ram (1100) until the thumb wheel (1176) of the threaded rod sits flush against the proximal end (1105) of the ram, as illustrated in FIG. 14B.

Optionally, an adjustable stop (250) can be attached to or inserted into the inserter. The adjustable stop (250) is inserted into the distal end of the inserter and a lug (252) located on the superior portion of the adjustable stop is mated into a mating pocket located on the superior portion of the inserter. An adjustment rod (260) affixed to the inserter is advanced through the lug (252) as shown in FIG. 2.

In a preferred embodiment, the adjustment rod (1156), which is attached to the proximal end of the adjustable stop (1150) as a portion thereof, is inserted at the distal end (820) of a protruding spring-loaded button (818) through the channel (823), as illustrated in FIG. 16. The thread (1166) of the adjustment rod (1156) engages a corresponding thread (825) on the inferior portion of the channel (823), allowing the adjustable stop to lock in reference to the proximal end of the inserter. Correct positioning of the adjustable stop is provided by inserting the head (1163) of the key tab (1158) on the inferior side of the adjustable stop into the distal end (830) of the keyhole slot (816) on the superior portion (817) of the inserter. Translational movement of the adjustable stop towards the proximal end of the inserter traps the head (1163) of the key tab on the inferior portion (849) of the proximal end (831) of the keyhole slot and locks the adjustable stop in place with respect to the inserter. Depressing the button (818) on the inserter allows the adjustable stop to be advanced axially along the inserter until it reaches a desired position, such as 0 mm (located at the unmarked setting 822a), 3 mm (822b), 6 mm (822c), or 9 mm (822d) (FIG. 9). The adjustable stop locks in position upon release of the button (818). Other, unmarked incremental settings may be achieved by rotating the thumb wheel (1176) as needed. The position of the threaded rod (1170) relative to the marked setting(s) indicates the depth of the implant from the anterior face of the vertebral body (FIG. 14B).

In a preferred embodiment, the superior portion of the inserter has a plurality of settings, the settings may contain one or more markings (422b, 822b; 422c, 822c; and 422d, 822d) at regular or irregular intervals to indicate the position of the inserter (or adjustable stop, if used), allowing for placement of an implant at the desired location between adjacent vertebral bodies, such as at a depth of 0 mm, 3 mm, 5 mm, 6 mm, 8 mm, or 9 mm, or other suitable locations between the adjacent vertebral bodies (FIGS. 2 and 9). Optionally one setting, such as the 0 mm setting, is unmarked (422a, 822a). In some embodiments, the adjustment rod (260) can be rotated using the ball driver (310), and thereby advanced axially along the inserter until it reaches a desired position, such as 0 mm (located at the unmarked setting (422a)), 3 mm (422b), 5 mm (422c), or 8 mm (422d) (FIG. 2).

B. Implant Insertion

With the jaw, ram and adjustable stop (if desired) in position, an implant (1300) of appropriate size can be introduced to the jaw. The practitioner can rotate the inserter knob (406, 806) towards the practitioner to progressively tighten the jaw prongs (460a, 460b, 860a, 860b), grabbing the anterior end of the implant, or the lateral end cap (1302) of the implant (1300), as shown in FIG. 19.

Figure 19:
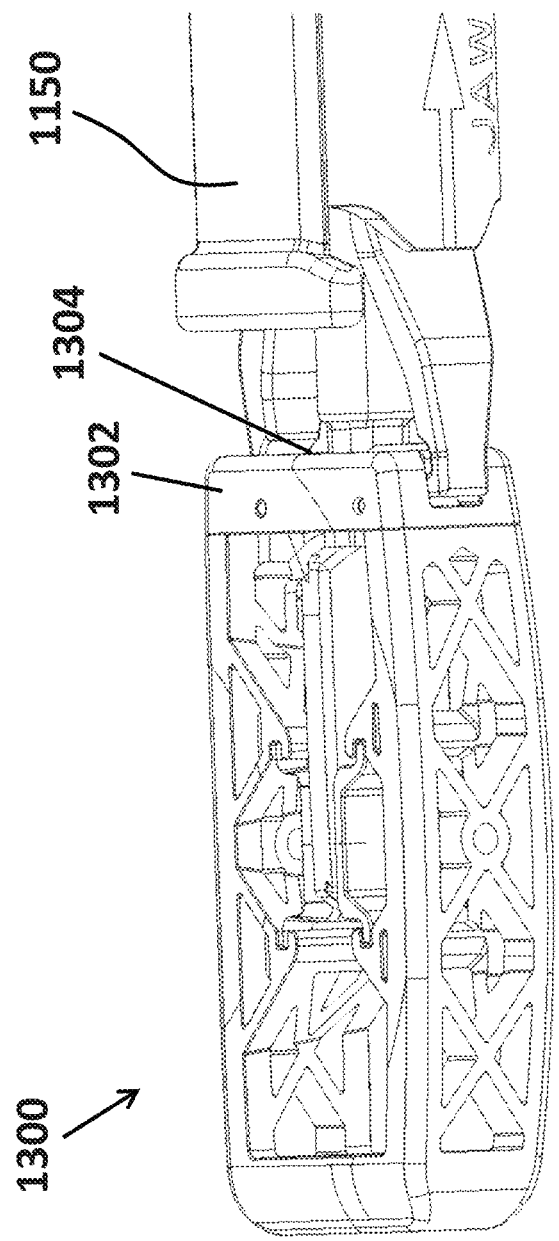
FIG. 19 shows a perspective view of an exemplary lateral implant attached to an inserter assembly.

The distal end of a fully assembled insertion system holding an exemplary implant is illustrated in FIG. 19.

In some embodiments, once the implant is securely fastened inside the jaw prongs, the ram (1000) is pushed until the head (1002) of the ram touches one or more strike plates of the implant. In other embodiments, the ram (1100) is pushed until it touches a ramp guide (1304) of the implant (1300) (FIG. 19) or other feature in the implant that is used to ensure that the blades are inside the implant (in an insertion position) and are not deployed prematurely prior to insertion of the implant in the desired site in a patient's spine.

Once the implant and ram are in their correct positions, an implant impaction cap (1200) can be threaded to the proximal end of the ram (1004, 1100) until it is positioned against the knob (406, 806) of the inserter (FIGS. 17A and 17B). Alternatively, the implant impaction cap (1200) threads into the proximal end (805) of the knob (806) via its distal threaded portion (1208) (FIGS. 17A, 17B). The flat surface (1201) of the proximal end (1203) of the impaction cap may be impacted to push the implant into a desired site between the adjacent vertebral bodies. Alternatively, the proximal end of the ram may be impacted directly to position the implant inside the vertebral body.

C. Impaction and Deployment of Blades

Figure 3:
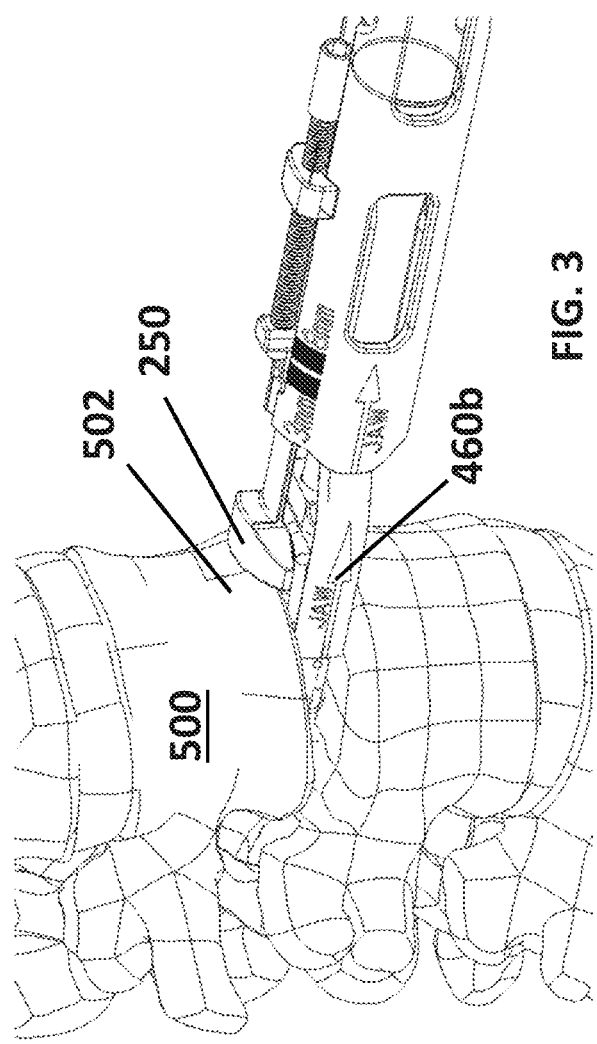
FIG. 3 shows a perspective view of an exemplary inserter assembly fully inserted between two adjacent vertebral bodies using an anterior approach.
Figure 20:
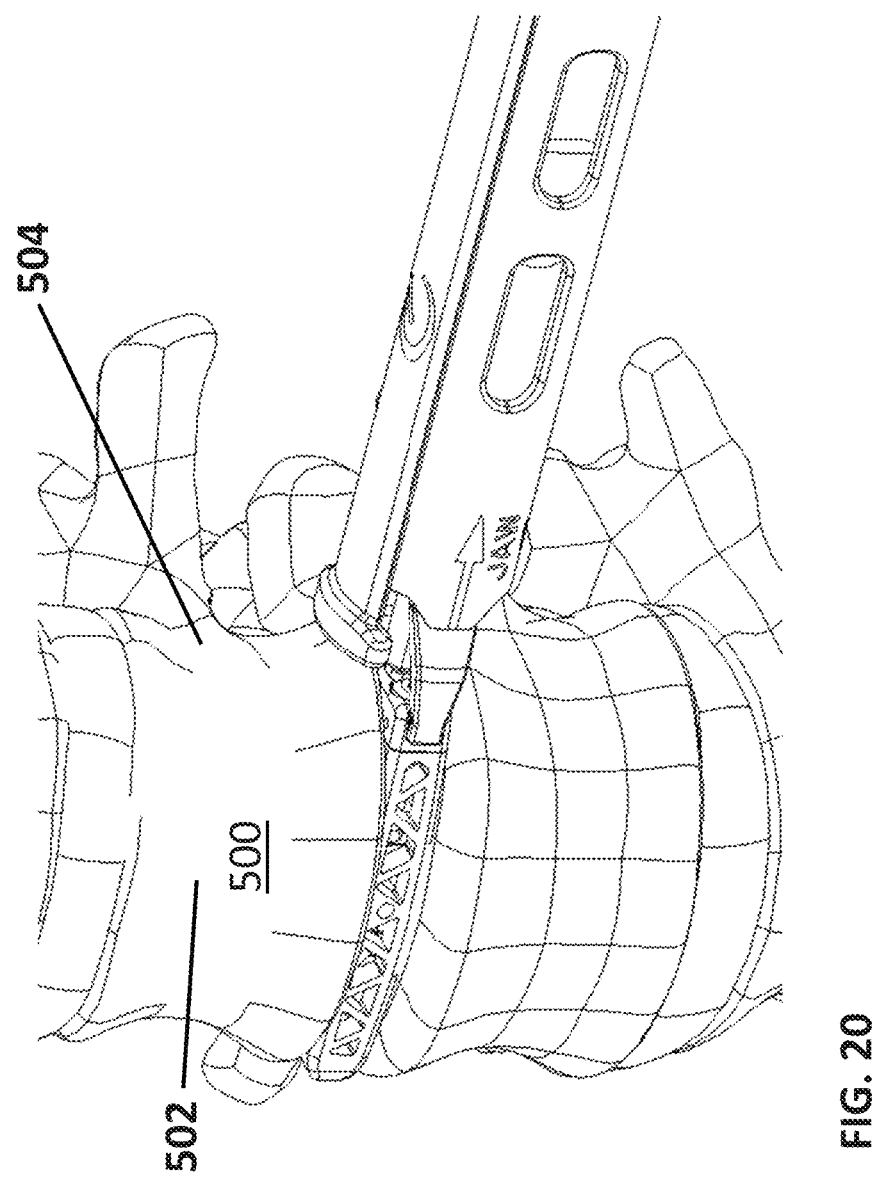
FIG. 20 illustrates an exemplary lateral implant fully inserted into the vertebral body.

At this point, the implant/inserter assembly can be impacted into the vertebral body (500) until the adjustable stop (250, 1150), if attached, contacts the anterior edge (502), or a lateral edge (504) of the vertebral body (FIGS. 3 and 20, respectively). The adjustable stop ensures proper placement of the implant, allowing for an implant depth of 0 mm, 3 mm, 5 mm, 6 mm, 8 mm, or 9 mm, or other suitable locations within between the adjacent vertebral bodies, as needed in various embodiments.

With the implant in position, the implant impaction cap (1200) may be removed by the practitioner and replaced with a ram impaction cap (1350) (FIG. 21A). The ram impaction cap allows translation of the ram (1000, 1100) when impacted. The ram can now be impacted with the aid of various visualization methods. In a preferred embodiment, fluoroscopy can be used. The flat surface (1351) of the proximal end (1353) of the ram impaction cap may be hit or impacted to thrust the blades (if present) in the implant into the superior and inferior vertebral bodies. For example, impaction of the ram impaction cap can deploy the blades (1307a, 1307b) of an implant, so that the blades protrude superiorly and inferiorly through the implant cage, as seen in FIG. 22.

In some embodiments, the pawl (410) allows for distal translation of the ram, but locks in place against a tooth in the tooth pattern in the absence of impaction. Upon impaction of the ram impaction cap, the blades of the implant are deployed, protruding superiorly and inferiorly through the implant cage, and the head (1002) of the ram (1000) is seated against and adjacent to the anterior end of the implant cage.

In some embodiments, the thumb wheel (1176) of the threaded rod (1170) may be tightened to advance the threaded rod into the implant. The implant blades may be deployed by turning the thumb wheel.

FIGS. 3 and 22 illustrate exemplary implant cages fully inserted into the vertebral body using anterior and lateral approaches, respectively. FIG. 22 shows the blades (1307a, 1307b) deployed superiorly and inferiorly relative to the body of the cage so that they are deployed in the superior and inferior vertebral bodies.

Counter-clockwise rotation of the inserter knob (406, 806) disengages the inserter from the implant, allowing for removal of the insertion assembly.

D. Installation of Cover Plate

In some embodiments, after the cage is inserted and deployed between the vertebral bodies, a cover plate is placed on the anterior end of the cage. Insertion of a cover plate on the anterior end of the implant cage prevents dislocation of the strike plates from the vertebral body.

Figure 5:
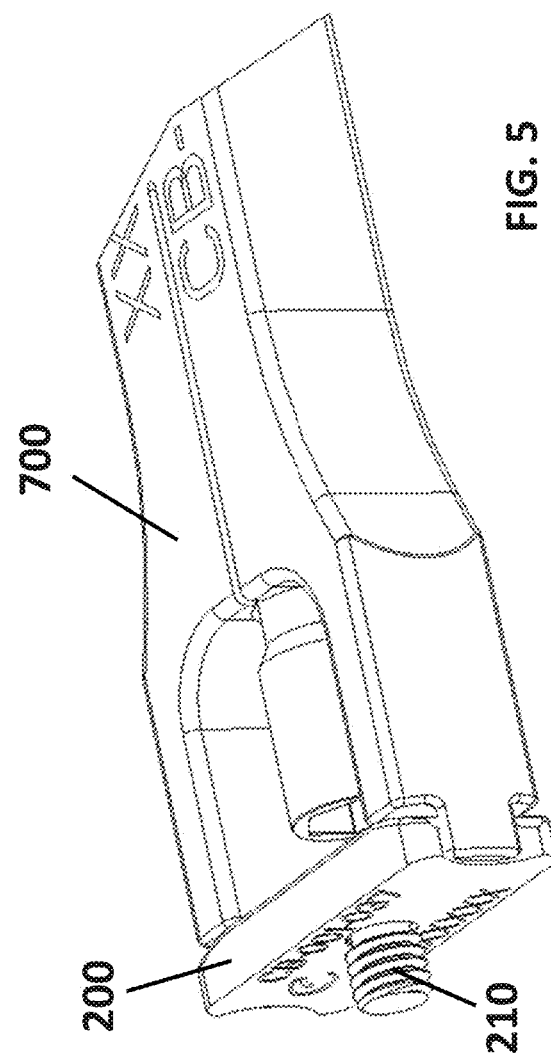
FIG. 5 shows a partial perspective view of the distal end of an exemplary cover plate inserter holding an exemplary cover plate and screw.

In some embodiments, a cover plate inserter tip (700) is threaded to the distal end (658) of a cover plate inserter (650). The cover plate inserter tip (700) is configured to clasp an implant cover plate (200), as illustrated in FIG. 5.

A socket driver (320) slides through the inserter tip (700) and inside the hollow body of the inserter (650), and can be attached to a driver handle, as shown in FIGS. 4A-4C. The head (322) of the socket driver is then inserted through the cover plate inserter until it protrudes through the cover plate inserter tip (700) and into a screw (210) that secures the cover plate (200) to the anterior end of the implant cage (FIG. 5). The head (not shown in figures) of the screw (210) is configured to fit inside and mate with a corresponding depression in the head (322) of the socket driver.

The socket driver and cover plate inserter are removed and the implant procedure is complete, leaving the implant in the desired location between the vertebral bodies, preferably with the blades on the implant deployed.

In other embodiments where a cover plate is not used, the blades may be secured in the deployed position using a lock screw and ball driver (310) (FIGS. 18A and 18B) or other suitable locking mechanisms.

E. Optional Reversion for Implant Removal or Re-Positioning

In some embodiments, the implant cage may be removed from its position in the spine using a removal tool (950). First, the cover plate (200) is removed by unscrewing the cover plate from the screw hole on the anterior end of the cage, exposing the threaded holes of the strike plates.

A removal tool (950) is attached to one of the strike plates, as shown in FIG. 6. The slap hammer attachment (952) on the removal tool is tapped using the back end of a mallet (900). Alternatively, a tuning fork or other suitable device may be used. The removal tool is removed, and the procedure is repeated on the other strike plate, if two strike plates are present in the implant. Optionally both strike plates may be pulled out of the superior and inferior vertebral bodies simultaneously, instead of sequentially, as described herein. For example, optionally two removal tools may be used in place of a single removal tool.

The resulting retraction of the strike plates pulls the blades into the body of the implant; allowing the practitioner to pull the implant out of, or adjust its position between the adjacent vertebral bodies without destroying the implant. Removal of the implant from the vertebral body occurs by attaching the implant removal tool (950) to the center threaded hole of the implant as seen in FIG. 6. The slap hammer attachment (952) of the implant removal tool (950) is tapped using the back end of a mallet (900), as seen in FIG. 6. Alternatively, a tuning fork or other suitable device may be used in place of a mallet.

In other embodiments, the implant cage may be removed from its position in the spine using the insertion system illustrated in FIG. 14B. Preferably, the insertion/removal tool assembly has an inserter, jaw, ram, and threaded rod. To remove the implant from its position in the spine, first, the lock screw is removed from the implant using a ball driver (310). The inserter jaws are attached to the implant by rotating the knob (806) counter-clockwise and tightening the thumb wheel (1176). The implant impaction cap (1200) is threaded into the proximal end (805) of the knob (806) via its distal threaded portion (1208) (FIGS. 17A, 17B). The handle portion (1204) of the implant impaction cap may be rotated clockwise to retract the blades into the body of the implant. This allows the practitioner to pull the cage out of, or adjust its position between the adjacent vertebral bodies without destroying the cage.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An intervertebral implant insertion system comprising an inserter, a jaw, and a ram;
   wherein the inserter comprises a hollow central cavity with a distal end and a proximal end;
   wherein the jaw comprises:
     i) a hollow shaft, and
     ii) a distal end and a proximal end;
   wherein the distal end of the jaw comprises one or more prongs;

wherein the ram has a suitable size and shape for insertion into the hollow shaft of the jaw;

wherein the shaft of the jaw fits inside the hollow central cavity of the inserter in slidable relation thereto;

further comprising an adjustable stop, wherein the adjustable stop establishes the relative depth of the implant between adjacent vertebral bodies;

wherein the adjustable stop comprises a proximal end configured to attach to the inserter, a body that extends along a superior surface of the inserter, and a stop portion located at a distal end of the body of the adjustable stop; and wherein the body of the adjustable stop further comprises a key tab that is configured to be inserted into a slot in the superior surface of the inserter.

2. The system of claim 1, wherein the proximal end of the jaw is hollow and connects with the hollow shaft.

3. The system of claim 1, wherein the body of the adjustable stop has a curvature that corresponds to the superior surface of the inserter.

4. The system of claim 1, further comprising an implant impaction cap, a ram impaction cap, or a combination thereof; wherein the implant impaction cap pushes the implant into a desired site between the adjacent vertebral bodies, and wherein the ram impaction cap deploys blades of the implant.

5. The system of claim 1, wherein the one or more prongs of the jaw are configured to hold an implant.

6. The system of claim 1, wherein the superior surface of the inserter further comprises a button that is configured to receive a portion of the adjustable stop.

7. The system of claim 1, wherein the superior surface of the inserter comprises one or more markings that correspond with insertion depths for an implant.

8. The system of claim 6, wherein the inserter further comprises a curved surface beneath the button, wherein the lower portion of the curved surface contains a plurality of grooves or threads, and wherein the upper portion of the curved surface is smooth.

9. The system of claim 4, wherein the implant impaction cap is configured to mate with the proximal end of the inserter for insertion or removal of the implant from between the vertebrae.

10. The system of claim 4, wherein the ram impaction cap is configured to mate with the proximal end of the ram for deployment or retraction of the implant blades.

11. The system of claim 10, wherein the ram impaction cap comprises a large proximal end and a hollow threaded shaft, wherein the ram impaction cap may be used to adjust the position of the implant blades in the vertebral body.

12. An implant insertion kit comprising the intervertebral implant insertion system of claim 1.

13. The kit of claim 12, further comprising an implant impaction cap, a ram impaction cap, or a combination thereof.

14. The kit of claim 13, further comprising a deployable implant cage.

15. The kit of claim 14, further comprising a cover plate.

16. The kit of claim 15, comprising a plurality of implant cages with deployable blades.

17. The kit of claim 15, wherein each cover plate has suitable dimensions to fit on the anterior end of one of the cages.

18. The kit of claim 17, wherein a single jaw is able to receive and mate with a plurality of different sized cages.

19. The kit of claim 18, wherein the width or spacing between the prongs of a jaw ranges from 15 mm to 30 mm.

20. A method of using an intervertebral implant insertion system comprising: an inserter, a jaw, and a ram; wherein the inserter comprises a hollow central cavity with a distal end and a proximal end; wherein the jaw comprises: i) a hollow shaft, and ii) a distal end and a proximal end; wherein the distal end of the jaw comprises one or more prongs; wherein the ram has a suitable size and shape for insertion into the hollow shaft of the jaw; and wherein the shaft of the jaw fits inside the hollow central cavity of the inserter in slidable relation thereto, the method comprising:

i) inserting the jaw into the inserter;
ii) inserting the ram into the jaw;
iii) inserting an implant between the one or more prongs of the jaw;
iv) introducing the implant into the desired position between vertebral bodies of a patient in need thereof; and
v) impacting the proximal end of the ram until the implant is positioned inside a vertebral body.

21. The method of claim 20, further comprising deploying blades of the implant.

22. The method of claim 20, further comprising attaching an adjustable stop onto a superior portion of the inserter until the adjustable stop contacts an adjacent vertebral body.

23. The method of claim 21, further comprising inserting a cover plate on the anterior end of the implant.

24. The method of claim 23, further comprising retracting the blades of the implant within the implant or back to their original position.

25. The method of claim 24, further comprising removing the implant from between the vertebral bodies.

* * * * *